(12) United States Patent
Murphy et al.

(10) Patent No.: US 10,034,823 B2
(45) Date of Patent: Jul. 31, 2018

(54) METHOD OF COLORING HAIR WITH WASHFAST BLUE IMIDAZOLIUM DIRECT DYE COMPOUNDS

(71) Applicant: Noxell Corporation, Hunt Valley, MD (US)

(72) Inventors: Bryan Patrick Murphy, Loveland, OH (US); Guiru Zhang, Lebanon, OH (US); Jielu Zhao, Mason, OH (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 15/267,585

(22) Filed: Sep. 16, 2016

(65) Prior Publication Data

US 2018/0078478 A1     Mar. 22, 2018

(51) Int. Cl.
- *A61Q 5/10*     (2006.01)
- *A61K 8/49*     (2006.01)
- *C09B 29/036*     (2006.01)

(52) U.S. Cl.
CPC .............. *A61K 8/4946* (2013.01); *A61Q 5/10* (2013.01); *C09B 29/0037* (2013.01); *C09B 29/0051* (2013.01); *A61K 2800/4324* (2013.01)

(58) Field of Classification Search
CPC ........ A61Q 5/10; A61Q 5/065; A61K 8/4946; A61K 8/4953; A61K 8/49; A61K 2800/434

See application file for complete search history.

(56) References Cited

U.S. PATENT DOCUMENTS

| | | | |
|---|---|---|---|
| 5,708,151 | A | 1/1998 | Mockli |
| 5,733,343 | A | 3/1998 | Mockli |
| 6,001,135 | A | 12/1999 | Rondeau et al. |
| 6,464,731 | B1 | 10/2002 | Genet et al. |
| 6,478,827 | B1 | 11/2002 | Genet et al. |
| 6,997,963 | B2 | 2/2006 | Guerin |
| 7,172,633 | B2 | 2/2007 | Samain et al. |
| 7,198,650 | B2 | 4/2007 | Pourille-Grethen et al. |
| 7,300,471 | B2 | 11/2007 | Greaves et al. |
| 7,507,260 | B2 | 3/2009 | Rondeau et al. |
| 7,513,917 | B2 | 4/2009 | Pasquier et al. |
| 7,794,509 | B2 | 9/2010 | Cremer et al. |
| 8,444,715 | B2 | 5/2013 | Lewis et al. |
| 8,758,451 | B2 | 6/2014 | Lewis et al. |
| 8,932,370 | B2 | 1/2015 | Lewis et al. |
| 9,248,086 | B2 | 2/2016 | Lewis et al. |
| 2002/0095732 | A1 | 7/2002 | Kravtchenko et al. |
| 2003/0106169 | A1 | 6/2003 | Vidal et al. |
| 2003/0177591 | A1 | 9/2003 | Mockli |
| 2004/0049020 | A1 | 3/2004 | Mockli |
| 2004/0107513 | A1 | 6/2004 | Vidal et al. |
| 2004/0168265 | A1 | 9/2004 | Eliu et al. |
| 2004/0187225 | A1 | 9/2004 | Vidal et al. |
| 2004/0244125 | A1 | 12/2004 | Mockli |
| 2005/0071933 | A1 | 4/2005 | Rondeau |
| 2005/0154195 | A1 | 7/2005 | Eliu |
| 2005/0191253 | A1 | 9/2005 | Gourlaouen et al. |
| 2006/0010617 | A1 | 1/2006 | Gourlaouen et al. |
| 2006/0016025 | A1 | 1/2006 | Greaves et al. |
| 2006/0026776 | A1 | 2/2006 | Mockli |
| 2006/0156490 | A1* | 7/2006 | David ................... A61K 8/4946 8/406 |
| 2006/0174423 | A1 | 8/2006 | Rothe et al. |
| 2007/0010663 | A1 | 1/2007 | David et al. |
| 2007/0125261 | A1 | 6/2007 | Daubresse et al. |
| 2007/0214580 | A1 | 9/2007 | Eliu et al. |
| 2009/0089939 | A1 | 4/2009 | Greaves et al. |
| 2009/0293208 | A1 | 12/2009 | Eliu et al. |
| 2011/0011417 | A1 | 1/2011 | Greaves et al. |
| 2011/0142892 | A1 | 6/2011 | Daly |
| 2012/0210520 | A1 | 8/2012 | Lim et al. |
| 2015/0101132 | A1 | 4/2015 | David et al. |
| 2015/0113742 | A1 | 4/2015 | David |
| 2016/0106648 | A1 | 4/2016 | Lewis et al. |
| 2016/0271030 | A1 | 9/2016 | Zhang et al. |

(Continued)

FOREIGN PATENT DOCUMENTS

| | | | |
|---|---|---|---|
| DE | 102010030434 A1 | 4/2011 | |
| DE | 102014223934 A1 * | 5/2016 | ............... A61Q 5/10 |

(Continued)

OTHER PUBLICATIONS

STIC Search Report dated Dec. 6, 2016.*
"U.S. Appl. No. 15/072,464, Non Final Office Action dated Jan. 9, 2017", 8 pgs .
"U.S. Appl. No. 15/072,464, Response filed Jul. 10, 2017 to Non Final Office Action dated Jan. 9, 2017", 7 pgs.
"U.S. Appl. No. 15/072,479, Non Final Office Action dated Jan. 6, 2017", 8 pgs .
"U.S. Appl. No. 15/072,479, Response filed Jul. 6, 2017 to Non Final Office Action dated Jan. 6, 2017", 7 pgs.
"U.S. Appl. No. 15/072,484, Non Final Office Action dated Jan. 6, 2017", 8 pgs .
"U.S. Appl. No. 15/072,484, Response filed Jul. 6, 2017 to Non Final Office Action dated Jan. 6, 2017", 7 pgs.
"U.S. Appl. No. 15/267,560, Non Final Office Action dated Jan. 6, 2017", 10 pgs.

(Continued)

*Primary Examiner* — Eisa B Elhilo
(74) *Attorney, Agent, or Firm* — Schwegman Lundberg & Woessner, P.A.

(57) ABSTRACT

Described herein is a method of dyeing the hair. The method includes applying to the hair a hair color composition including one or more direct dye compounds and rinsing the hair with water. The one or more direct dye compounds each include a blue-violet or blue chromophore, one or two permanent cations, one to four incipient cations, and one or more hydrophobic moieties. The incipient cations are pendant to the core structure and are neutral. The direct dye compounds enter the hair shaft after the hair color composition is applied to the hair. The hair color composition has a pH of from about 6 to about 11. The pH of the hair after rinsing is from about 3.5 to about 6. The rinsing of the hair causes one or more of the one to four incipient cations to change from neutral to positively charged inside of the hair shaft.

10 Claims, No Drawings

(56) References Cited

U.S. PATENT DOCUMENTS

2016/0271040 A1 9/2016 Zhang et al.
2016/0271041 A1 9/2016 Zhang et al.
2016/0271042 A1 9/2016 Zhang et al.

FOREIGN PATENT DOCUMENTS

| DE | 102014223934 A1 | 5/2016 |
|----|----|----|
| EP | 0850636 A1 | 7/1998 |
| EP | 1574205 A2 | 9/2005 |
| EP | 1619221 A1 | 1/2006 |
| EP | 1757660 A1 | 2/2007 |
| EP | 2359909 A2 | 8/2011 |
| FR | 2855967 A1 | 12/2004 |
| WO | WO-95/01772 A1 | 1/1995 |
| WO | WO-97/20545 A1 | 6/1997 |
| WO | WO-02/31056 A1 | 4/2002 |
| WO | WO-02/078596 A2 | 10/2002 |
| WO | WO-03/032937 A1 | 4/2003 |
| WO | WO-03/072657 A1 | 9/2003 |
| WO | WO-2004/000257 A2 | 12/2003 |
| WO | WO-2005/095522 A2 | 10/2005 |
| WO | WO-2006/134051 A1 | 12/2006 |
| WO | WO-2013/058817 A1 | 4/2013 |
| WO | WO-2016/149429 A1 | 9/2016 |
| WO | WO-2016/149430 A1 | 9/2016 |
| WO | WO-2016/149431 A1 | 9/2016 |
| WO | WO-2016/149432 A1 | 9/2016 |

OTHER PUBLICATIONS

"U.S. Appl. No. 15/267,560, Response filed Jul. 6, 2017 to Non Final Office Action dated Jan. 6, 2017", 8 pgs.
"International Application Serial No. PCT/US2016/022727, International Search Report dated Jun. 16, 2016", 8 pgs.
"International Application Serial No. PCT/US2016/022727, Written Opinion dated Jun. 16, 2016", 10 pgs.
"International Application Serial No. PCT/US2016/022728, International Search Report dated Jun. 10, 2016", 7 pgs.
"International Application Serial No. PCT/US2016/022728, Written Opinion dated Jun. 10, 2016", 11 pgs.
"International Application Serial No. PCT/US2016/022729, International Search Report dated Jun. 10, 2016", 7 pgs.
"International Application Serial No. PCT/US2016/022729, Written Opinion dated Jun. 10, 2016", 8 pgs.
"STIC Search Report", (Jul. 24, 2017), 20 pgs.
"U.S. Appl. No. 15/072,464, Notice of Allowance dated Aug. 16, 2017", 8 pgs.
"U.S. Appl. No. 15/072,479, Notice of Allowance dated Aug. 28, 2017", 9 pgs.
"U.S. Appl. No. 15/072,484, Corrected Notice of Allowance dated Aug. 23, 2017", 4 pgs.
"U.S. Appl. No. 15/072,484, Notice of Allowance dated Aug. 7, 2017", 7 pgs.
"U.S. Appl. No. 15/072,496, Corrected Notice of Allowance dated Sep. 11, 2017", 2 pgs.
"U.S. Appl. No. 15/072,496, Non Final Office Action dated Jan. 19, 2017", 7 pgs.
"U.S. Appl. No. 15/072,496, Notice of Allowance dated Aug. 22, 2017", 10 pgs.
"U.S. Appl. No. 15/072,496, Response filed Jul. 18, 2017 to Non Final Office Action dated Jan. 19, 2017", 5 pgs.
"U.S. Appl. No. 15/267,560, Notice of Allowance dated Aug. 1, 2017", 7 pgs.
"International Application Serial No. PCT/US2016/022730, International Search Report dated Jun. 9, 2016", 3 pgs.
"International Application Serial No. PCT/US2016/022730, Written Opinion dated Jun. 9, 2016", 8 pgs.
"STIC Search Report", (Aug. 3, 2017), 189 pgs.
"U.S. Appl. No. 15/267,560, Corrected Notice of Allowance dated Feb. 5, 2018", 2 pgs.
"U.S. Appl. No. 15/267,560, Corrected Notice of Allowance dated Feb. 9, 2018", 2 pgs.
"International Application Serial No. PCT/US2017/051408, International Search Report dated Nov. 29, 2017", 8 pgs.
"International Application Serial No. PCT/US2017/051408, Written Opinion dated Nov. 29, 2017", 8 pgs.
"U.S. Appl. No. 15/267,560, Notice of Allowability dated Jan. 22, 2018", 4 pgs.
"European Application Serial No. 16712642.4, Response filed May 25, 2018 to Communication pursuant to Rules 161(1) and 162 EPC dated Nov. 16, 2017", w/ English Claims, 14 pgs.

* cited by examiner

METHOD OF COLORING HAIR WITH WASHFAST BLUE IMIDAZOLIUM DIRECT DYE COMPOUNDS

TECHNICAL FIELD OF THE INVENTION

Provided is a method of dyeing the hair and other keratinaceous material with one or washfast blue-violet to blue imidazolium azo direct dye compounds. The direct dye compounds each have one to four incipient cations. A decrease in pH when rinsing the hair causes one or more of the incipient cations to change from neutral to positively charged inside of the hair shaft. Also provided are haircolor compositions comprising the imidazolium azo compounds that may serve as hair dyes, and methods of using the same. These materials can be used with or without oxidant.

BACKGROUND OF THE INVENTION

In general, direct dye products last only 6-10 shampoos and are hence known as semi-permanent. However, many consumers want more permanent results, and therefore default to oxidative dye products that contain hydrogen peroxide or other oxidants. Providing vibrant blue-violet to blue colors is challenging, because many of the vibrant dyes are not sufficiently stable for permanent haircolor compositions, and those that are stable to hair dyeing conditions are not sufficiently vibrant. The direct dye compounds and the method described herein can be used in either direct dye or oxidation dye products.

The permanent alteration of the color of keratinous fibers, in particular human hair, by the application of hair dyes is well known. In order to provide the consumer with the shade, longevity, and the intensity of color desired, an oxidative coloring process involving complex chemical reactions is utilized. Permanent hair dyeing formulations typically comprise primary intermediates (also known as oxidative hair dye precursors or developers) and couplers (also known as color modifiers or secondary intermediates). These dye precursors are sufficiently small, polar and soluble to diffuse into the hair shaft where, once activated by an oxidizing agent under basic conditions, such as hydrogen peroxide, the primary intermediates react with other dye precursors, e.g., couplers, to form larger colored chromophores in the hair shaft. The chromophores formed in the hair shaft do not readily diffuse out of the hair during subsequent washing with water and/or detergents because they are bigger, less polar and soluble than dye precursors that diffused in.

Hair colorant products are typically sold in the form of kits containing a dye component (e.g., a dye solution) and an oxidizing component (e.g., a hydrogen peroxide solution). In use, the dye component is mixed with the oxidizing component and the resultant mixture is applied to hair. When the two components are mixed, oxidizing agents present in the oxidizing component begins to oxidize primary intermediates present in the dye component and the oxidized primary intermediates begin to react with couplers to form chromophores. Since coloring hair is one of the beauty routines, it is highly desirable that the dyeing process, excluding bleaching, be rather a physical process, which would allow it to be aligned with many other beauty routines such as applying lip color and facial touchups. The challenge is to still meet all of the other requirements of hair color (e.g., washfastness, resistance to perspiration, little or no bleeding of color from the hair when it is wet, evenness, etc.).

Many attempts have been made by the hair color industry to enhance the washfastness of direct dyes by either forming a covalent bond between chromophore and proteins inside hair or increasing the number of binding sites, typically cationic centers, on the chromophore. However, each attempt has its drawbacks. The approach through covalent bonding does not differentiate proteins in hair from skin. The approach through multiple binding sites on the dyes (i.e. multiple positive charges to interact with negative sites on hair, either by bonding several monocationic dyes together or by installing multiple cationic centers on a single chromophore) runs into the obstacles of uneven color due to uneven damage (negative charges) along the length of the hair fibers and reduced dye penetration into hair fibers because the dyes are typically at least twice as large as common oxidative dye precursors. An increase in the number of binding sites minimizes bleeding and color loss caused by rinsing by providing stronger hair-chromophore interactions. However, the same strong binding force to the cuticle also prevents the chromophores from penetrating deep into the cortex of hair, because it is difficult for dyes with multiple positive charges to diffuse through negatively charged networks of keratin proteins. Additionally, since polycationic dyes remain bound to the hair surface rather than penetrating into the fiber, it is difficult to produce dark shades, due to limited binding sites on the surface of hair.

In general, blue-violet to blue colors used for dyeing or hueing agents for materials such as plastics, fabrics, and hair are either fused polycyclics such as triarylmethanes, substituted phenoxazines and anthraquinones, carbocyclic azo dyes in which the acceptor half of the molecule is highly substituted with electron-withdrawing groups used to shift the color into the desired range, bis(azo) compounds that extend conjugation, or azo dyes that have a carbocyclic donor portion and a thiazolium or thiazole (substituted with electron-withdrawing groups such as cyano or nitro) acceptor portion. Considering the donor-acceptor approach of color design, the well-known tactics are to include powerful election-withdrawing groups in the acceptor end of the molecule, thus pulling electron density towards the acceptor portion, driving the color to higher absorbance wavelengths. Although it can give the desired color shift, it can decrease the stability of the dyes, particularly when the acceptor end is a heterocycle such as imidazolium or thiazolium.

Although these well-known and well-accepted aforementioned classes of dyes provide the blue-violet to blue colors desired, each of these classes has at least one flaw that makes it inappropriate for dyeing at alkaline pH in highly aqueous systems, such as in hair dye products or highly aqueous dyebaths. (More aqueous dyebaths are desired to decrease the environmental impact relative to dyebaths that use high levels of organic solvents.) The solubility, fastness properties, or stability of current materials may be insufficient for the applications. In cases in which solubility, resistance to removal by washing and perspiration, and stability are sufficient, the current materials do not have the required blue hue. Specifically in applications such as hair dyeing, this is an important outage.

Thiazolium and thiazole azo compounds in particular provide brilliant colors with high intensity. However, it is well-known that particularly for the vibrant and water soluble thiazolium dyes, stability is poor. Common, commercial imidazolium dyes (analogs of the thiazolium dyes) can give brilliant and stable orange to violet-red colors. However, there are no good examples of blue imidazolium dyes, most likely because using the common approach of adding electron-withdrawing groups to the acceptor (imidazolium) end of the molecule results in materials that are highly unstable, especially at alkaline pH.

Baumann and Dehnert described generating a violet imidazolium azo dye (in *Chimia* 15, 1961, 163-168) however they could not obtain blues, and Abbot, et al. (in *J. Phys. Chem. J. Phys. Chem. A* 2013, 117, 1853-1871) demonstrated the inherent instability of thiazolium compounds under basic conditions, making them unsuitable for applications for which neutral to alkaline pH is necessary.

Accordingly, there is a need for a direct dye compound with improved washfastness without the drawbacks previously described, and these imidazolium azo dyes meet all the criteria of color, stability, and fastness to be used as permanent hair dye compounds.

SUMMARY OF THE INVENTION

Described herein is a method of dyeing fibers, particularly keratin fibers, and most particularly hair, the method comprising (a) applying to the hair a hair color composition comprising one or more direct dye compounds, the one or more direct dye compounds each comprising (i) a blue-violet or blue chromophore; and (ii) one or two permanent cations, wherein the permanent cations are part of the chromophore, and wherein the chromophore and the permanent cations form a core structure; (iii) one to four incipient cations, wherein the incipient cations are pendant to the core structure, and wherein the incipient cations are neutral; and (iv) optionally one or more C2-C9 hydrophobic moieties, wherein the one or more C2-C9 hydrophobic moieties are pendant to the core structure; wherein the one or more direct dye compounds enter the hair shaft after the hair color composition is applied to the hair; and wherein the hair color composition has a pH of from about 6 to about 11; (b) rinsing the hair with water; wherein the pH of the hair after rinsing is from about 3.5 to about 6. Unlike completely carbocycle-based azo dyes in the blue-violet to blue range, the hair color compositions described herein can have high solubility in aqueous systems.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. When more than one composition is used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

As used herein, the term "hair" to be treated may be "living" i.e. on a living body or may be "non-living" i.e. in a wig, hairpiece or other aggregation of non-living keratinous fibers. Mammalian, particularly human, hair is preferred. However, wool, fur, and other keratin containing fibers are suitable substrates for the compositions according to the present invention.

As used herein, the term "pendant group" means a group of atoms attached to the core structure or chromophore. As described herein, the pendant group itself is not colored although it may influence the color of the chromophore. The pendant group may be further classified as an anchoring group or a hydrophobic group. A hydrophobic group is typically a carbon chain. An anchoring group is a group attached to either a permanent cation or incipient cation, occasionally it is attached to both a permanent cation and one or more incipient cations.

As used herein, the term "chromophore" means the part of the direct dye compound responsible for its color.

As used herein, the term "direct dye compound" means a dye used in a process in which dye molecules are attracted by physical forces at the molecular level to a textile or substrate such as the hair. As opposed to oxidative dyes, there is no chemical reaction required to form the chromophore. Additionally, there is no covalent bond formation between the direct dye and the substrate as opposed to reactive dyes. The direct dye compound does not undergo a chemical transformation before and after the dyeing process.

As used herein, the term "core structure" means the chromophore including one or two permanent cations that are pendant to the chromophore or part of the chromophore. In an embodiment, the chromophore is charged. In an embodiment, the chromophore is not charged as the permanent cation is pendant to the chromophore.

As used herein, the term "pendant" means when a functional group is linked to a core structure via covalent bond.

As used herein, the term "incipient cation" means a functional group that goes from neutral to positively charged due to protonation during a change in pH.

The hair colorant compositions of the present invention comprise one or more washfast direct dyes, optionally, oxidative dyes as well.

With regards to the direct dye compounds described herein, numerous tautomeric compounds may be involved. Thus, for example, 2-mercaptopyridine (I) may exist under known conditions in the pyridine-2-thione tautomer form (II).

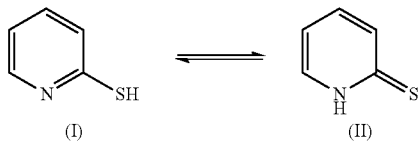

It is to be understood that when this development refers to a particular structure, all of the reasonable additional tautomeric structures are included. In the art, tautomeric structures are frequently represented by one single structure and the method described herein follows this general practice.

It is also understood that within the scope of this invention, E, Z isomers may be involved. Thus, for example, (E)-diphenyldiazene (III) converts under known conditions to (Z)-diphenyldiazene (IV), which is also reversible.

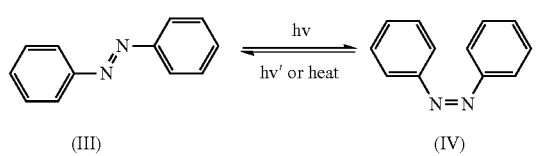 [SMILES: c1ccc(/N=N/c2ccccc2)cc1 ; c1ccc(/N=N\c2ccccc2)cc1]

It is to be understood that when this development refers to a particular structure, all of the reasonable additional E, Z isomers are included.

I. Washfast Blue-Violet or Blue Direct Dyes

Described herein is a method of dyeing the hair, the method comprising (a) applying to the hair a hair color composition comprising one or more blue-violet or blue direct dye compounds; the one or more direct dye compounds each comprising (i) a chromophore; (ii) one or two permanent cations, wherein the permanent cations are pendant to the chromophore or part of the chromophore, and wherein the chromophore and the permanent cations form a core structure; and (iii) one to four incipient cations, wherein the one to four incipient cations are pendant to the core structure, and wherein the incipient cations are neutral; and (iv) optionally one or more C2-C9 hydrophobic moieties, wherein the one or more C2-C9 hydrophobic moieties are pendant to the core structure; wherein the one or more direct dye compounds enter the hair shaft after the hair color composition is applied to the hair; and wherein the hair color composition has a pH of from about 6 to about 11; (b) rinsing the hair with water; wherein the pH of the hair after rinsing is from about 3.5 to about 6; and wherein the rinsing of the hair causes one or more of the one to four incipient cations to change from neutral to positively charged inside of the hair shaft.

In an embodiment, the hair color composition has a pH of from about 6 to about 11, alternatively from about 7 to about 11, alternatively from about 6 to about 9, alternatively from about 7 to about 9, and alternatively from about 9 to about 11.

The one to four incipient cations, typically an amino group or groups, are attached to the chromophore in addition to the existing permanent cation(s) to overcome the problems encountered in previous attempts to make cationic direct dyes more washfast. The chromophore would typically carry only one or two permanent positive charges such as quaternary ammonium salts, pyridinium, imidazolium, thiazolium, oxazolium, triazolium, pyrimidinium, triazinium, tetrazolium phenoxazinium, phenazinium or an analogous cation under basic conditions for typical hair color applications. The amino group(s) can remain mostly neutral under dyeing conditions (pH 10~11) because the typical $pK_a$ of aliphatic amines falls between 9~10.5. The dye would carry only one or two cationic charges under dyeing conditions, which provides the needed affinity (Coulombic attraction) for optimized uptake without preventing penetration due to relatively low charge density compared to polycationic dyes. However, once the coloring application is done and hair is rinsed, pH inside hair drops back to its natural pH, which is acidic, the amino group(s) attached to the chromophore would be protonated to become an ammonium cation, which adds one or more binding sites to the chromophore. The pH change functions as a convenient switch to turn on additional binding group(s) to make the chromophores more washfast. Primary amines work the best when compared to secondary and tertiary amines for the following two reasons: 1. primary amines resist oxidation by hydrogen peroxide, while secondary and tertiary amines can be oxidized and lose their anchoring capability when used together with a bleaching agent; 2. the protonated primary ammonium cation is the smallest in size, which allows stronger interaction with anions on hair compared to secondary and tertiary amines with more steric hindrance. The following are examples of washfast dyes wherein one or more incipient cations change from neutral to positively charged due a change of pH. It is to be understood that the order and relative extent of protonation of the individual amines is a function of their specify pKa. Additionally, there is a variety of possible identities and arrangements of substituents, and the schemes below are for illustrative purposes, and not exhaustive of the possibilities:

1)

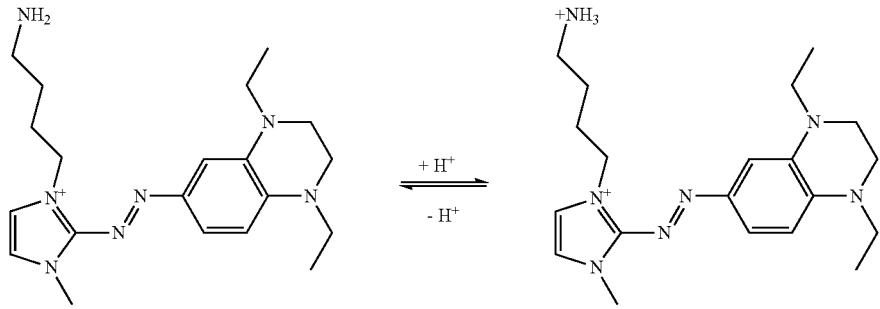

2)

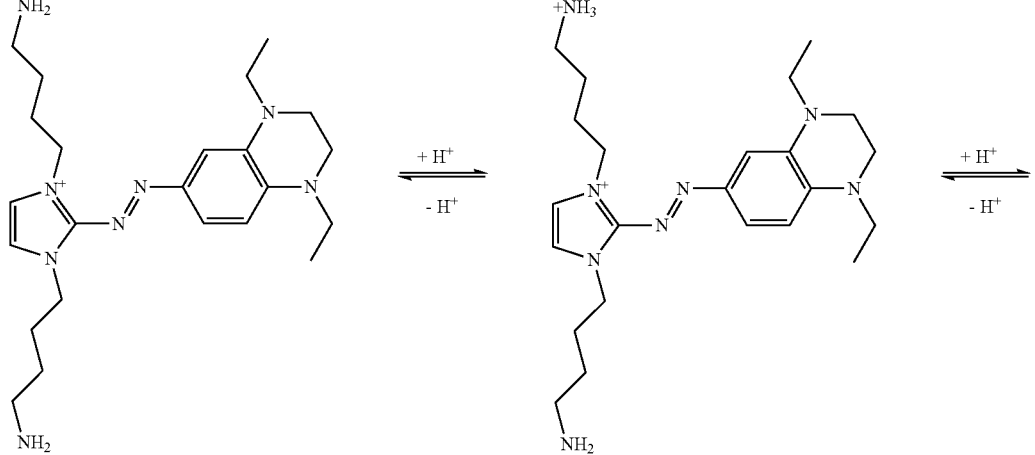

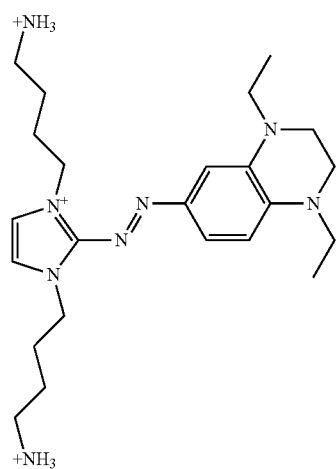
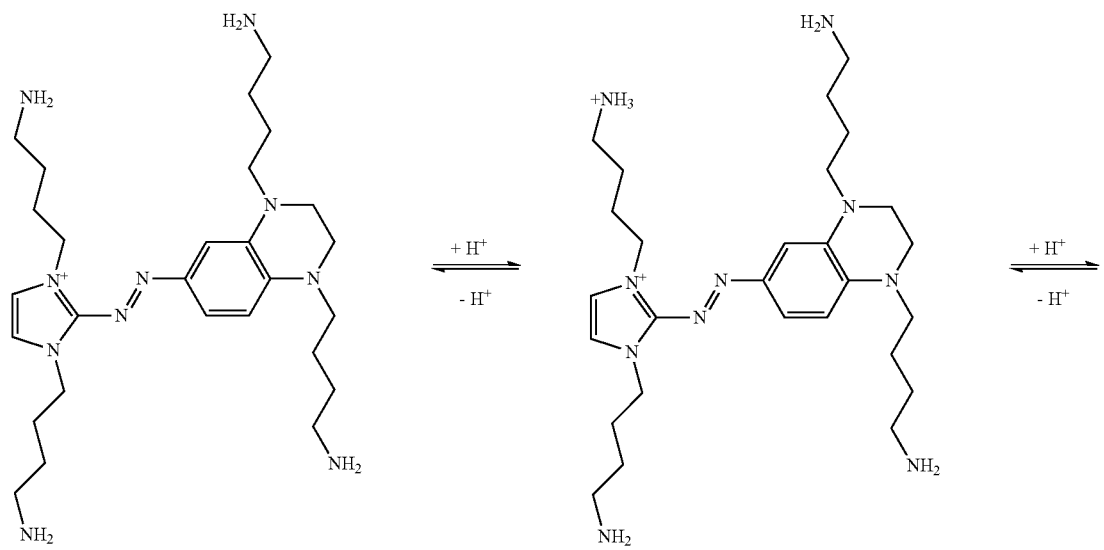
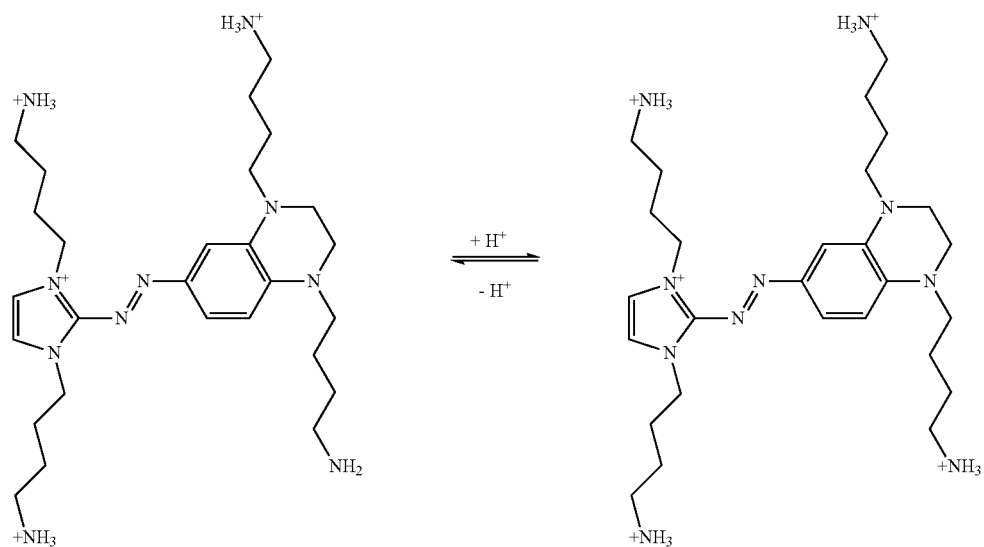

3)
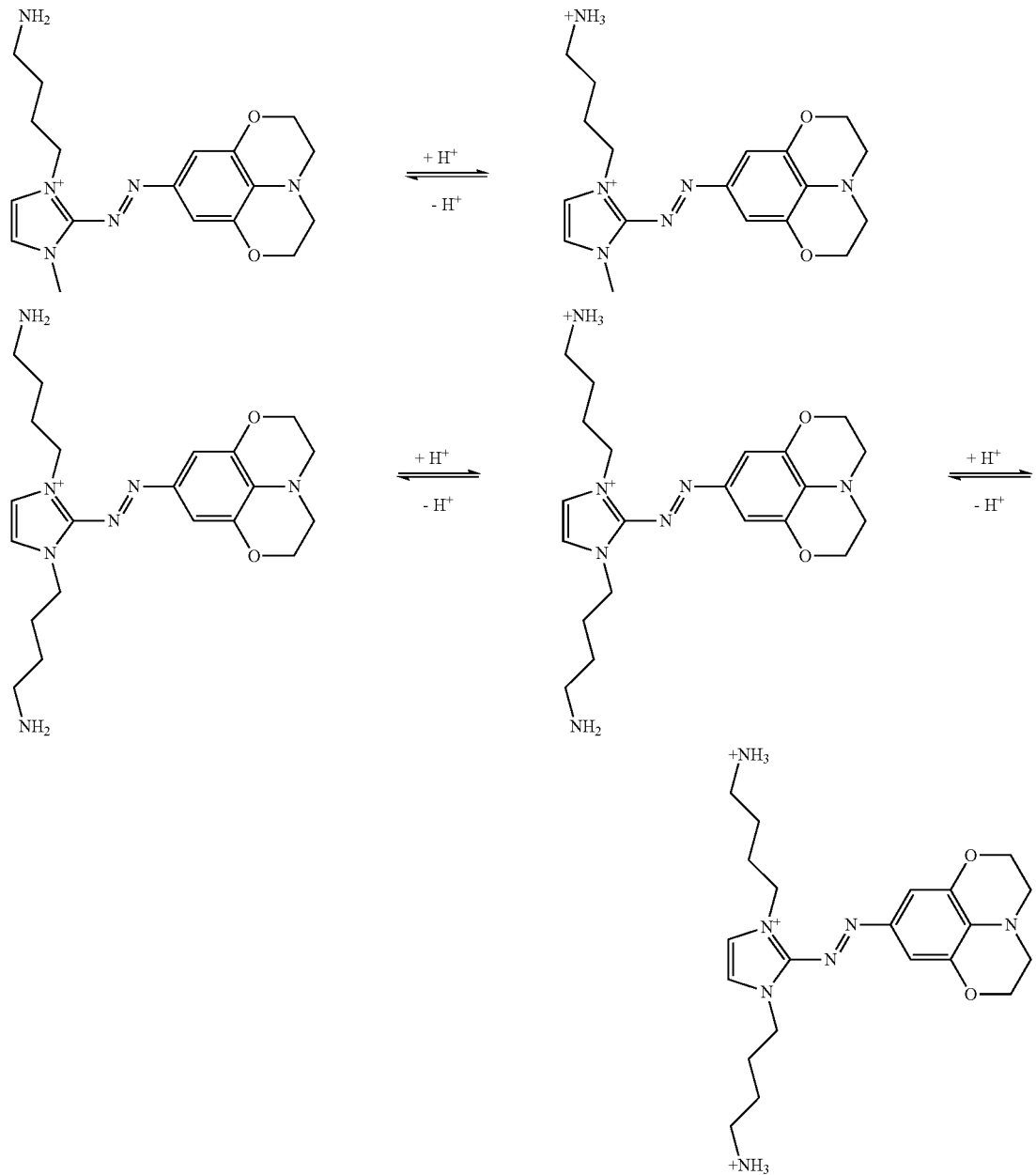
5)
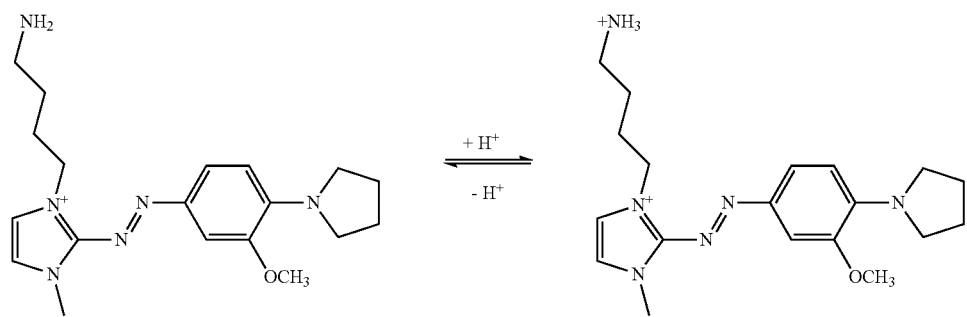

6)

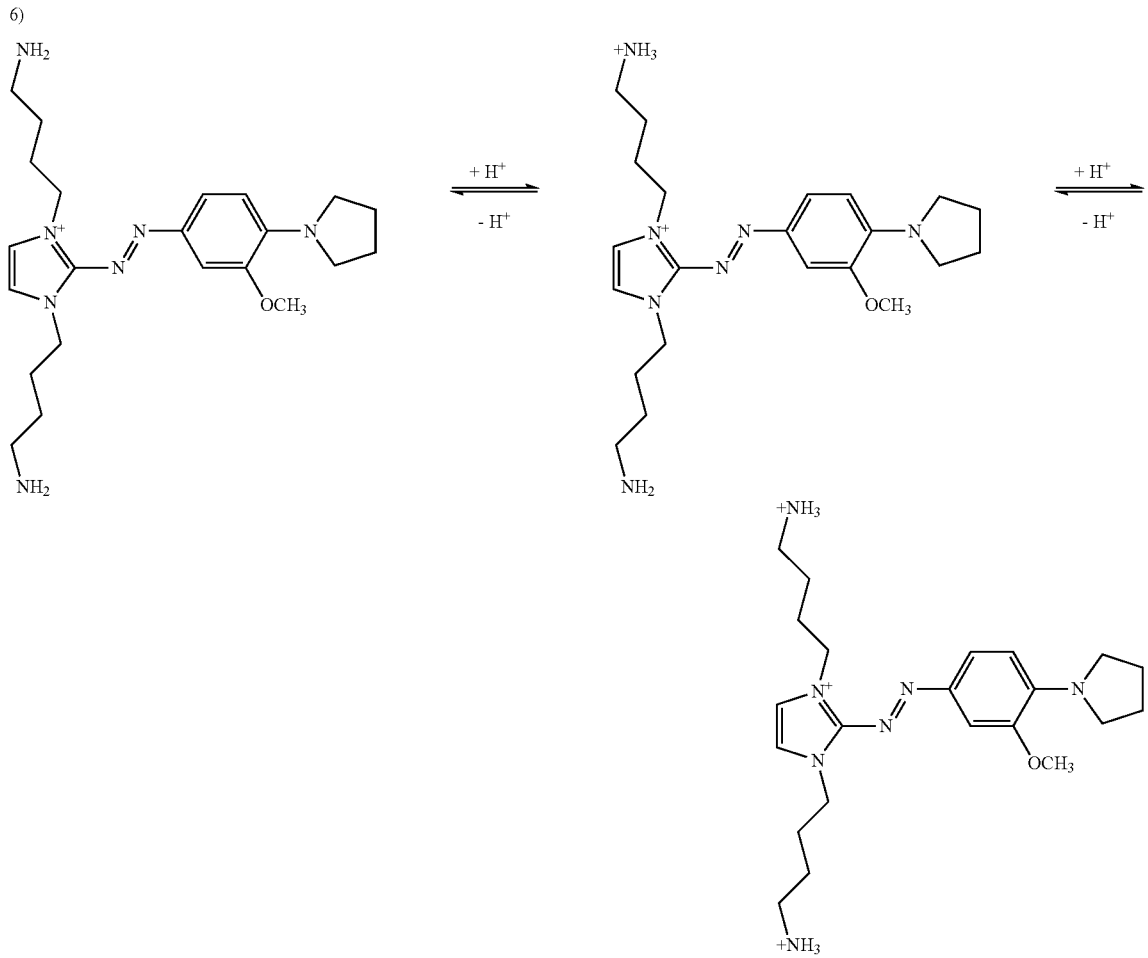

The linker groups, typically linear alkyl groups, would also function as modulators for the overall hydrophobicity of the dye. One of the common drawbacks of using exclusively cationic direct dyes for shading is off-tone fading as different dyes would be washed off hair at different rates, causing undesirable gradual color shift over time. Our technical approach minimizes off-tone fading by designing dyes of different colors with identical charge patterns with similar overall hydrophobicity. Additionally, the fact that these dyes are far more washfast than typical cationic dyes also contributes to minimal color lost and on-tone fading.

The direct dye compounds may be substituted with one permanent cationic charge, alternatively two permanent cationic charges. The direct dye compounds may comprise and one to four terminal amino groups and derivatives thereof, alternatively two terminal amino groups and derivatives thereof, and alternatively one terminal amino group and derivatives thereof, according to the following formula:

The chemical formulas of the blue-violet or blue direct dye compounds can be represented in the following ways, but not limited to what is shown below:

$(L_2)_y\text{-}C^*(\text{-}L_1\text{-}A)_n Z^-$ (V)

$(A_1\text{-}L_1\text{-})_n C^*(\text{-}L_2\text{-}A_2)_m L_3)_y Z^-$ (VI)

$(Q^*\text{-}L_3\text{-})_x C(\text{-}L_1\text{-}A_1)_m (\text{-}L_2\text{-}A_2)_n (L_4)_y (Z^-)_x$ or $Z^{x-}$ (VII)

$(L_3)_y\text{-}C(\text{-}L_1\text{-}Q^*(\text{-}L_2\text{-}A)_m)_n (Z^-)_n$ or $Z^{n-}$ (VIII)

$(L_2)_y\text{-}C^*(\text{-}L_1\text{-}A_1\text{-}(L_3\text{-}A_2)_m)_n Z^-$ (IX)

wherein

C is a chromophore;

Q* is an organic cation;

* stands for a permanent cationic charge, it can also be part of a chromophore bearing a cationic charge;

L is a linker or hydrophobic chain and;

A is the anchoring group, the fastness enhancer. It is typically a primary, secondary or tertiary amino group, preferably a primary amine. It is also a switch to allow the anchor to go between neutral and charged states when the pH in the surrounding environment changes.

Z is a counter anion. It is typically a halide, sulfate, methylsulfate, hydrogen sulfate, phosphate, hydrogen phosphate, dihydrogen phosphate, nitrate, perchlorate, tetrafluoroborate, hexafluorophosphate, triflate, acetate, formate or hydroxide.

n=1~4; m=1~4; n+m≤4; x=1~2; y=0~2.

In some embodiments, the compound is of Formula X, or a tautomer or salt . . . thereof

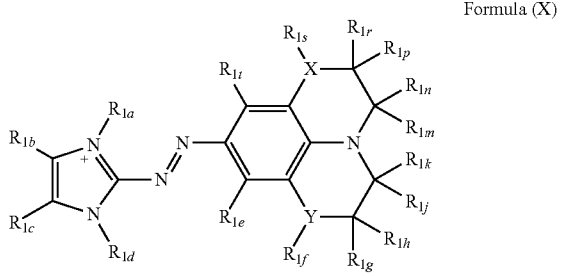

Formula (X)

wherein
(i) $R_{1g}$, $R_{1h}$, $R_{1j}$, $R_{1k}$, $R_{1m}$, $R_{1n}$, $R_{1p}$ and $R_{1r}$ are each independently hydrogen, alkyl, halogen substituted alkyl, alkenyl, alkynyl, aryl, hydroxyalkyl, aminoalkyl, alkyl group carrying a quaternary ammonium cation, carboxyl, alkoxy, aryloxy, acyl, halogen, nitro, nitroso, cyano, a heterocyclic moiety, thioether, thiol with a linker group, alkylsulfonate, alkylsulfate, carboxylalkyl, acrylamide or substituted acrylamides with or without a linker group, vinylsulfone with or without a linker group, sulfonyl ethyl sulfate with or without a linker group, halo-s-triazines with or without a linker group, halopyrimidines with or without a linker group, haloquinoxalines with or without a linker group;
(ii) $R_{1b}$, $R_{1c}$, $R_{1e}$ and $R_{1t}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group;
(iii) $R_{1f}$ and $R_{1s}$ are each independently hydrogen, alkyl, halogen substituted alkyl, alkenyl, alkynyl, aryl, hydroxyalkyl, aminoalkyl, alkyl group carrying a quaternary ammonium cation, acyl, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group;
(iv) $R_{1a}$ and $R_{1d}$ are each independently alkyl, halogen substituted alkyl, alkenyl, alkynyl, aryl, hydroxyalkyl, aminoalkyl, alkyl group carrying a quaternary ammonium cation, alkyl group carrying a quaternary ammonium cation, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group; and X and Y are each independently an oxygen or a nitrogen atom and when X or Y is a nitrogen atom the other can be a carbon atom; wherein in the case where X and/or Y is oxygen atom, the corresponding group attached to the oxygen atom, $R_{1f}$ and/or $R_{1s}$, ceases to exist. In some embodiments for compounds of Formula (X), at least one of X and Y is an oxygen atom, in some embodiments both X and Y are oxygen atoms. In some embodiments, $R_{1a}$, $R_{1d}$, $R_{1f}$ and $R_{1s}$ are each independently alkenyl, alkyl, aminoalkyl or alkyl group carrying a quaternary ammonium cation, in some embodiments the compound of Formula (X) is attached to a polymer through $R_{1a}$, $R_{1d}$, $R_{1f}$ and $R_{1s}$. In some embodiments, $R_{1b}$, $R_{1c}$, $R_{1e}$, $R_{1f}$, $R_{1g}$, $R_{1h}$, $R_{1j}$, $R_{1k}$, $R_{1m}$, $R_{1n}$, $R_{1p}$ and $R_{1r}$ are each independently hydrogen or alkyl.

In other embodiments, the compound is of Formula (XI), or a tautomer or salt thereof;

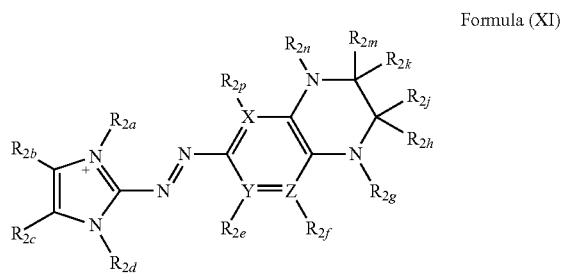

Formula (XI)

wherein
(i) $R_{2h}$, $R_{2j}$, $R_{2k}$ and $R_{2m}$ are each independently hydrogen, alkyl, halogen substituted alkyl, alkenyl, alkynyl, aryl, hydroxyalkyl, aminoalkyl, alkyl group carrying a quaternary ammonium cation, carboxyl, alkoxy, aryloxy, acyl, halogen, nitro, nitroso, cyano, a heterocyclic moiety, thioether, thiol with a linker group, alkylsulfonate, alkylsulfate, carboxylalkyl, acrylamide or substituted acrylamides with or without a linker group, vinylsulfone with or without a linker group, sulfonyl ethyl sulfate with or without a linker group, halo-s-triazines with or without a linker group, halopyrimidines with or without a linker group, haloquinoxalines with or without a linker group;
(ii) $R_{2b}$, $R_{2c}$, $R_{2e}$, $R_{2f}$ and $R_{2p}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group;
(iii) $R_{2g}$ and $R_{2n}$ are each independently hydrogen, alkyl, halogen substituted alkyl, alkenyl, alkynyl, aryl, hydroxyalkyl, aminoalkyl, alkyl group carrying a quaternary ammonium cation, acyl, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group;
(iv) $R_{2a}$ and $R_{2d}$ are each independently alkyl, halogen substituted alkyl, alkenyl, alkynyl, aryl, hydroxyalkyl, aminoalkyl, alkyl group carrying a quaternary ammonium cation, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group; and (v) X, Y and Z are each independently a carbon or a nitrogen atom; wherein the total number of nitrogen atoms among X, Y and Z equals to 0 or 1; the total number of carbon atoms among X, Y and Z equals to 2 or 3; and, in the case where one of X, Y, Z is a nitrogen atom, the corresponding group attached to the nitrogen atom, one of $R_{2e}$, $R_{2f}$ or $R_{2p}$, ceases to exist.

In some embodiments for compounds of Formula (XI), $R_{2g}$ and $R_{2n}$ are each independently hydrogen, alkenyl, alkyl, aminoalkyl or an alkyl group carrying a quaternary ammonium cation; in some embodiments $R_{2g}$ is hydrogen, alkenyl or alkyl and $R_1$, is alkenyl or alkyl.

In some embodiments, $R_{2a}$ and $R_{2d}$ are each independently alkenyl, alkyl, aminoalkyl or alkyl group carrying a quaternary ammonium cation; in some embodiments one or both of $R_{2a}$ and $R_{2d}$ are an alkyl group; in some embodiments $R_{2a}$ is alkyl and $R_{2d}$ is aminoalkyl or an alkyl group carrying a quaternary ammonium cation; in some embodiments one or both of $R_{2a}$ and $R_{2d}$ are an alkyl group carrying a quaternary ammonium cation.

In some embodiments, $R_{2b}$, $R_{2c}$, $R_{2e}$, $R_{2f}$ and $R_{2p}$ are each independently hydrogen or alkyl; in some embodiments $R_{2b}$, $R_{2c}$, $R_{2e}$, $R_{2f}$ and $R_{2p}$ are all hydrogen.

In some embodiments, $R_{2h}$, $R_{2i}$, $R_{2j}$ and $R_{2k}$ are each independently hydrogen and alkyl; in some embodiments, $R_{2h}$, $R_{2j}$, $R_{2k}$, and $R_{2m}$ are hydrogen.

In some embodiments, at least two of X, Y and Z are carbon; in some embodiments X, Y and Z are all carbon.

In other embodiments, the compound is of Formula (XII), or a tautomer or salt thereof;

Formula (XII)

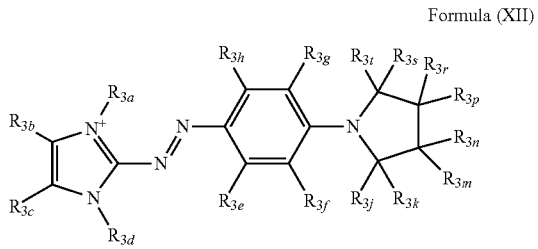

wherein (vi) $R_{3j}$, $R_{3k}$, $R_{3m}$, $R_{3n}$, $R_{3p}$, $R_{3r}$, $R_{3s}$, and $R_{3t}$ are each independently hydrogen, alkyl, halogen substituted alkyl, alkenyl, alkynyl, aryl, hydroxyalkyl, aminoalkyl, alkyl group carrying a quaternary ammonium cation, carboxyl, alkoxy, aryloxy, acyl, halogen, nitro, nitroso, cyano, a heterocyclic moiety, thioether, thiol with a linker group, alkylsulfonate, alkylsulfate, carboxylalkyl, acrylamide or substituted acrylamides with or without a linker group, vinylsulfone with or without a linker group, sulfonyl ethyl sulfate with or without a linker group, halo-s-triazines with or without a linker group, halopyrimidines with or without a linker group, haloquinoxalines with or without a linker group;

(vii) $R_{3b}$, $R_{3c}$, $R_{3e}$, $R_{3f}$, $R_{3g}$, and $R_{3h}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group;

(viii) $R_{3a}$ and $R_{3d}$ are each independently alkyl, halogen substituted alkyl, alkenyl, alkynyl, aryl, hydroxyalkyl, aminoalkyl, alkyl group carrying a quaternary ammonium cation, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group; and In some embodiments, $R_{3a}$ and $R_{3d}$ are each independently alkenyl, alkyl, aminoalkyl or alkyl group carrying a quaternary ammonium cation; in some embodiments one or both of $R_{3a}$ and $R_{3d}$ are an alkyl group; in some embodiments $R_{3a}$ is alkyl and $R_{3d}$ is aminoalkyl or an alkyl group carrying a quaternary ammonium cation; in some embodiments one or both of $R_{3a}$ and $R_{3d}$ are an alkyl group carrying a quaternary ammonium cation.

In some embodiments, $R_{3b}$, $R_{3c}$, $R_{3e}$, $R_{3f}$, $R_{3g}$, and $R_{3h}$ are each independently hydrogen or alkyl; in some embodiments $R_{3b}$, $R_{3c}$, $R_{3e}$, $R_{3f}$, $R_{3g}$, and $R_{3h}$ are all hydrogen.

In some embodiments, $R_{3j}$, $R_{3k}$, $R_{3m}$, $R_{3h}$, $R_{3n}$, $R_{3p}$, $R_{3r}$, $R_{3s}$, and $R_{3t}$ are each independently hydrogen and alkyl; in some embodiments, $R_{3j}$, $R_{3k}$, $R_{3m}$, $R_{3h}$, $R_{3n}$, $R_{3p}$, $R_{3r}$, $R_{3s}$, and $R_{3t}$ are hydrogen.

The following are examples of the synthesis of various washfast direct dye compounds as described herein:

Example 1

In example 1, (E)-1,3-bis(3-ammoniopropyl)-2-((1,4-diethyl-1,2,3,4-tetrahydro-quinoxalin-6-yl)diazenyl)-1H-imidazol-3-ium bromide dichloride is prepared from tetrahydroquinoxaline and 2-aminoimidazole.

Synthesis of
1,4-diethyl-1,2,3,4-tetrahydroquinoxaline

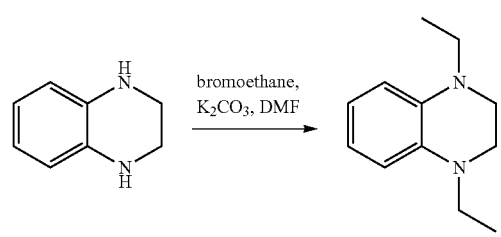

A mixture of tetrahydroquinoxaline (20.13 g), potassium carbonate (62.19 g) and bromoethane (49.04 g) in 120 mL of DMF is stirred at room temperature for 48 hours. The reaction mixture is filtered. Chromatography on silica gel yields 1,4-diethyl-1,2,3,4-tetrahydroquinoxaline as a yellow oil (16 g).

Synthesis of (E)-6-((1H-imidazol-2-yl)diazenyl)-1,4-diethyl-1,2,3,4-tetrahydroquinoxaline

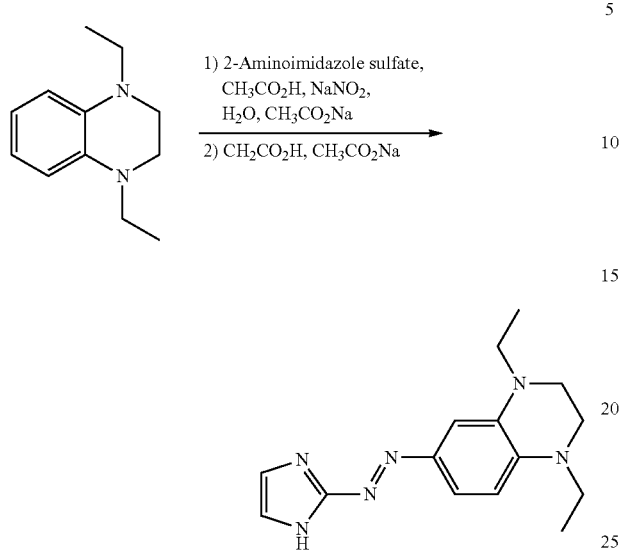

2-Aminoimidazole sulfate (11.6 g) is dissolved in 7.4 mL of concentrated HCl, 8 mL of water, and 40 mL of acetic acid. The resulting solution is cooled to 0° C. To the solution is added a solution of 6.08 g of $NaNO_2$ in 16 mL of water dropwise where the internal temperature is maintained under 5° C. The resulting yellow-brown solution is stirred for 30 minutes at 0° C. In a separate flask equipped with a mechanical stirrer a mixture of 1,4-diethyl-1,2,3,4-tetrahydroquinoxaline, 13.1 g of sodium acetate and 40 mL of acetic acid is cooled to 0° C. To this slurry is added the diazonium solution slowly and the internal temperature of the reaction is maintained below 5° C. After the addition is complete, the resulting violet suspension is stirred for 1 hour at 0° C. The dark reaction mixture is poured into a large beaker containing 400 g ice. Aqueous NaOH (20%) is added to the suspension slowly until pH 6.5 is reached. The mixture is extracted with dichloromethane 6 times to yield crude (E)-6-((1H-imidazol-2-yl)diazenyl)-1,4-diethyl-1,2,3,4-tetrahydroquinoxaline (19.5 g, impure). This material is used in the next step without further purification.

Synthesis of (E)-2-((1,4-diethyl-1,2,3,4-tetrahydroquinoxalin-6-yl)diazenyl)-1,3-bis(3-(2,2,2-trifluoroacetamido)propyl)-1H-imidazol-3-ium bromide

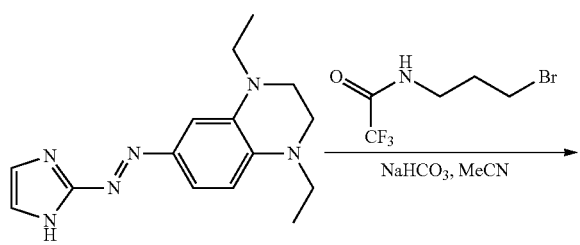

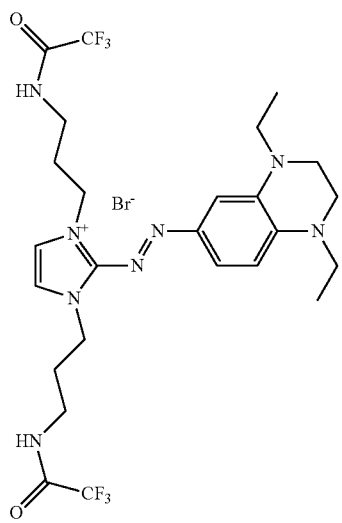

Crude (E)-6-((1H-imidazol-2-yl)diazenyl)-1,4-diethyl-1,2,3,4-tetrahydroquinoxaline (19.5 g) is dissolved in 150 mL of dry acetonitrile. $NaHCO_3$ (20.2 g) and 3-bromopropylamine trifluoroacetamide (37.4 g) are added and the mixture is stirred under reflux for 7 hours. The reaction mixture is filtered and concentrated. The resulting residue is purified by chromatography and triturated with cold acetone to yield pure (E)-2-((1,4-diethyl-1,2,3,4-tetrahydroquinoxalin-6-yl)diazenyl)-1,3-bis(3-(2,2,2-trifluoroacetamido)propyl)-1H-imidazol-3-ium bromide (9.6 g).

Synthesis of (E)-1,3-bis(3-ammoniopropyl)-2-((1,4-diethyl-1,2,3,4-tetrahydroquinoxalin-6-yl)diazenyl)-1H-imidazol-3-ium bromide dichloride

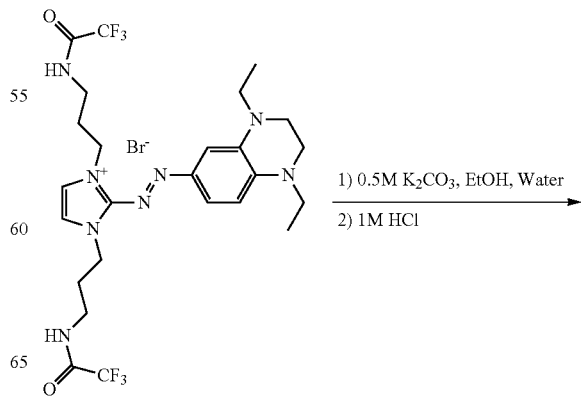

-continued

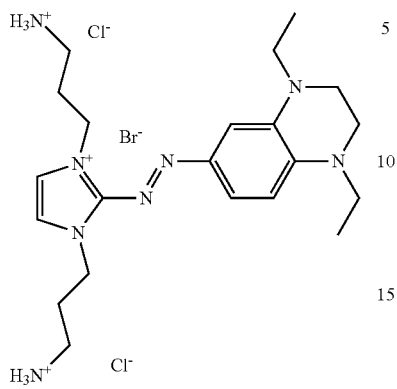

To a solution of 5.37 g (E)-2-((1,4-diethyl-1,2,3,4-tetrahydroquinoxalin-6-yl)diazenyl)-1,3-bis(3-(2,2,2-trifluoroacetamido)propyl)-1H-imidazol-3-ium bromide in 256 mL of ethanol is added 64 mL of 0.5 M $K_2CO_3$ solution. The resulting aqueous mixture is stirred at 40° C. for 24 hours. The reaction is cooled to room temperature and poured in to a large beaker. 1M HCl is added to adjust the solution to pH 7. Ethanol is removed by concentrating under vacuum at 35° C. The resulting aqueous dye solution is washed with dichloromethane 5 times and concentrated under reduced pressure to produce (E)-1,3-bis(3-ammoniopropyl)-2-((1,4-diethyl-1,2,3,4-tetrahydroquinoxalin-6-yl)diazenyl)-1H-imidazol-3-ium bromide dichloride.

Example 2

In example 2, (E)-2-((1,4-diethyl-1,2,3,4-tetrahydroquinoxalin-6-yl)diazenyl)-1,3-bis(3-(trimethyl-ammonio)propyl)-1H-imidazol-3-ium tribromide is prepared from tetrahydroquinoxaline and 2-aminoimidazole.

Synthesis of (E)-2-((1,4-diethyl-1,2,3,4-tetrahydroquinoxalin-6-yl)diazenyl)-1,3-bis(3-(trimethyl-ammonio)propyl)-1H-imidazol-3-ium tribromide

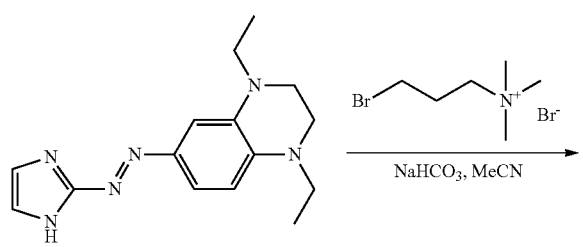

A mixture of (E)-6-((1H-imidazol-2-yl)diazenyl)-1,4-diethyl-1,2,3,4-tetrahydroquinoxaline (1 g), (3-bromopropyl) trimethyl ammonium bromide (2.75 g), and 886 mg of sodium bicarbonate in 10 mL acetonitrile is stirred under reflux for 5 hours. The reaction mixture is filtered and the dark solid collected is washed with acetonitrile and dried. The dark powder is then suspended in dry methanol and filtered to remove insoluble salt. The blue filtrate is concentrated under vacuum to yield 1.1 g of (E)-2-((1,4-diethyl-1,2,3,4-tetrahydroquinoxalin-6-yl)diazenyl)-1,3-bis(3-(trimethyl-ammonio)propyl)-1H-imidazol-3-ium tribromide.

Example 3

In example 3 (E)-2-((1-methyl-4-(2,2,2-trifluoroacetyl)-1,2,3,4-tetrahydroquinoxalin-6-yl)-diazenyl)-1,3-bis(3-(2,2,2-trifluoroacetamido)propyl)-1H-imidazol-3-ium bromide is prepared from tetrahydroquinoxaline and 2-aminoimidazole.

Synthesis of 1-(3,4-dihydroquinoxalin-1(2H)-yl)-2,2,2-trifluoroethan-1-one

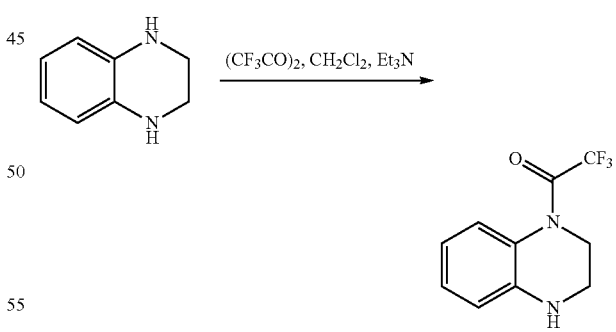

A round bottom flask is charged with 1.34 g of tetrahydroquinoxaline, 10 mL of dichloromethane and 1.11. g of trimethylamine. The reaction mixture is cooled in an ice bath and 1.94 g of trifluoroacetic anhydride is added dropwise. The resulting mixture is stirred at 0° C. for 30 minutes and then warmed up to room temperature. After filtration the solution obtained is dried and the residue is purified with silica gel chromatography. 1-(3,4-dihydroquinoxalin-1(2H)-yl)-2,2,2-trifluoroethan-1-one is obtained as white solid (1.01 g).

Synthesis of 2,2,2-trifluoro-1-(4-methyl-3,4-dihydroquinoxalin-1(2H)-yl)ethan-1-one

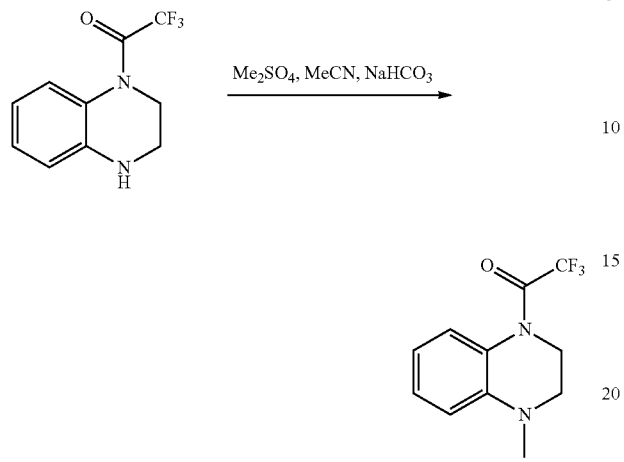

To a mixture of 1-(3,4-dihydroquinoxalin-1(2H)-yl)-2,2,2-trifluoroethan-1-one (920 mg) and 672 mg of NaHCO$_3$ in 20 mL of acetonitrile is added 504 mg of dimethyl sulfate slowly. The mixture is heated at 85° C. for 10 hours. The crude material is filtered and concentrated, and the residue is purified by column chromatography to produce the 2,2,2-trifluoro-1-(4-methyl-3,4-dihydroquinoxalin-1(2H)-yl)ethan-1-one as yellow oil (820 mg).

Synthesis of (E)-1-(7-(1H-imidazol-2-yl)diazenyl)-4-methyl-3,4-dihydroquinoxalin-1(2H)-yl)-2,2,2-trifluoroethan-1-one

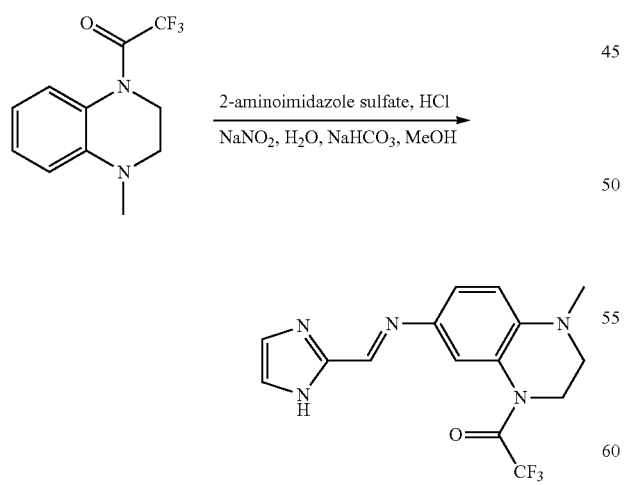

A solution of 158 mg of 2-aminoimidazole sulfate in 0.4 mL of concentrated HCl and 0.4 mL of water is cooled to 0° C. To this solution is added dropwise a solution of 82.8 mg of NaNO$_2$ in 0.6 mL of water. The resulting yellow solution is as stirred at 0° C. for 30 minutes and is added slowly to a suspension of 244 mg of 2,2,2-trifluoro-1-(4-methyl-3,4-dihydroquinoxalin-1(2H)-yl)ethan-1-one and 504 mg of NaHCO$_3$ in 3 mL of MeOH. The reaction mixture turns red. After the addition is complete, the mixture is filtered and the orange solid collected is dried to yield the crude product, (E)-1-(7-((1H-imidazol-2-yl)diazenyl)-4-methyl-3,4-dihydroquinoxalin-1(2H)-yl)-2,2,2-trifluoroethan-1-one. This material is used in the next step without further purification.

Synthesis of (E)-2-((1-methyl-4-(2,2,2-trifluoroacetyl)-1,2,3,4-tetrahydroquinoxalin-6-yl)-diazenyl)-1,3-bis(3-(2,2,2-trifluoroacetamido)propyl)-1H-imidazol-3-ium bromide

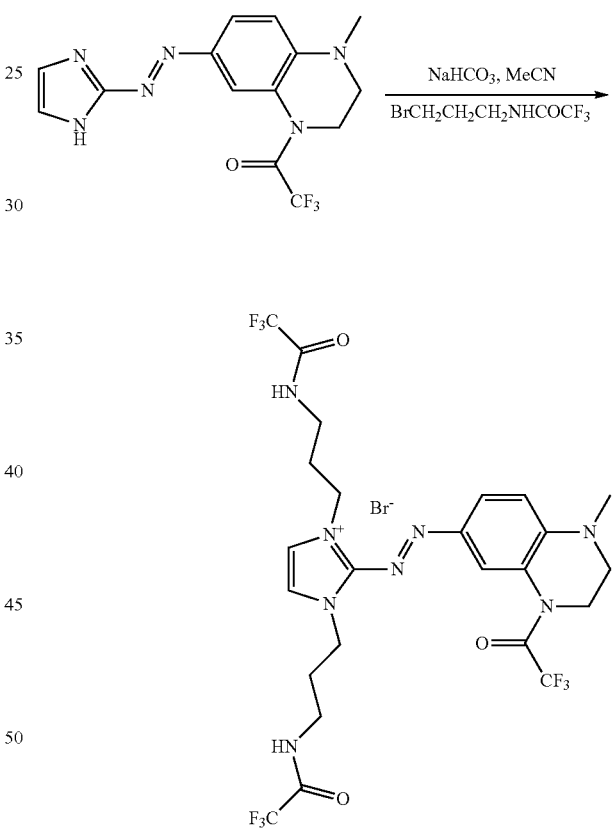

A mixture of crude (E)-1-(7-((1H-imidazol-2-yl)diazenyl)-4-methyl-3,4-dihydroquinoxalin-1(2H)-yl)-2,2,2-trifluoroethan-1-one 260 mg, 194 mg of NaHCO$_3$ and 540 mg of 3-bromopropylamine trifluoroacetamide is heated in 5 mL of MeCN at 86° C. for 16 hours. The reaction mixture is filtered and the filtrate is concentrated and the resulting residue is purified with column chromatography to yield 380 mg of (E)-2-((1-methyl-4-(2,2,2-trifluoroacetyl)-1,2,3,4-tetrahydroquinoxalin-6-yl)diazenyl)-1,3-bis(3-(2,2,2-trifluoroacetamido)-propyl)-1H-imidazol-3-ium bromide.

Synthesis of (E)-1,3-bis(3-ammoniopropyl)-2-((1-methyl-1,2,3,4-tetrahydroquinoxalin-6-yl)diazenyl)-1H-imidazol-3-ium bromide dichloride

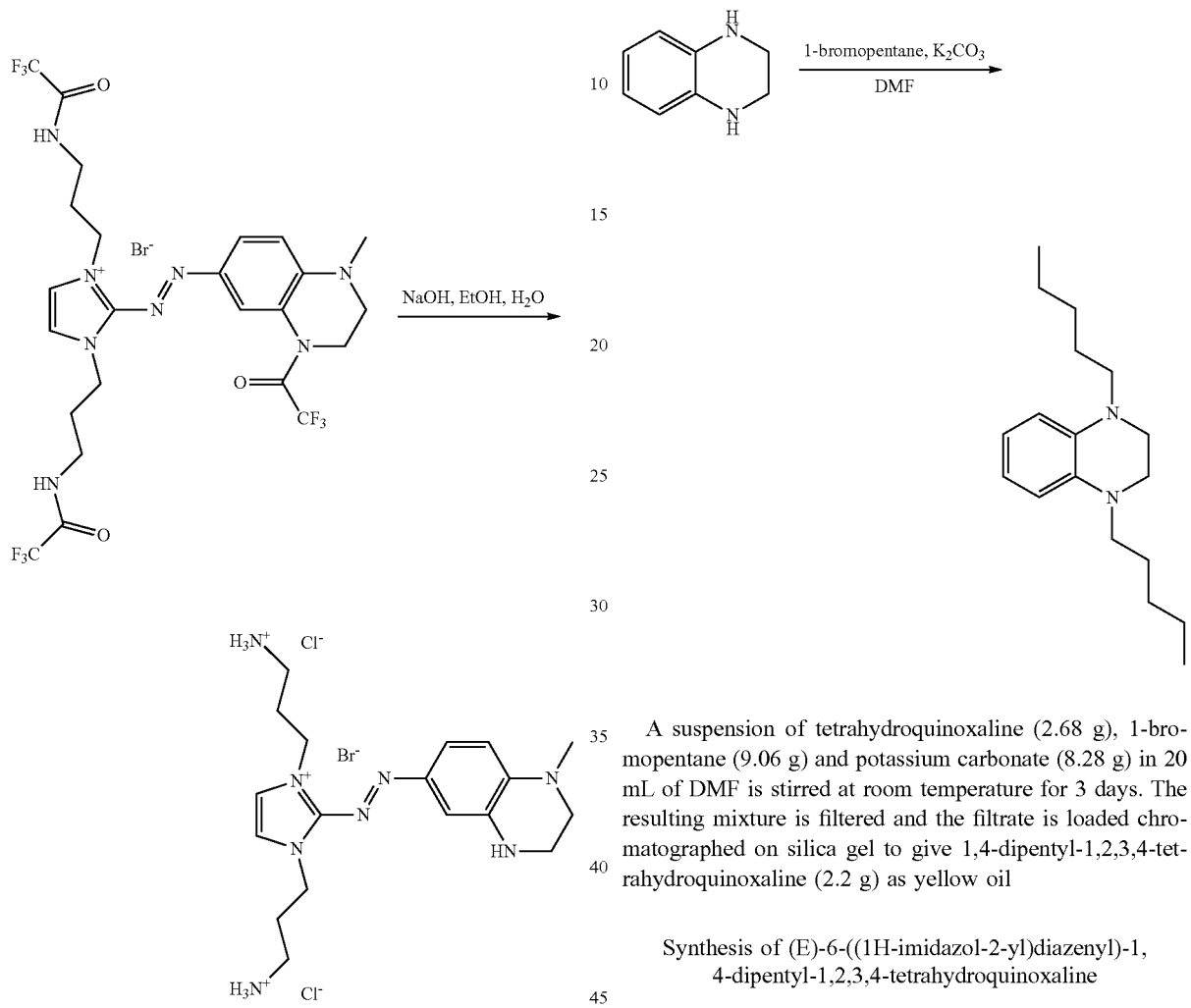

A mixture of (E)-2-((1-methyl-4-(2,2,2-trifluoroacetyl)-1,2,3,4-tetrahydroquinoxalin-6-yl)diazenyl)-1,3-bis(3-(2,2,2-trifluoroacetamido)-propyl)-1H-imidazol-3-ium bromide (330 mg), 3.64 mL of 0.5 M NaOH and 14.5 mL of ethanol is stirred at room temperature until deprotection is complete. The pH of the reaction solution is adjusted to pH 7.0 with 1M HCl. The resulting solution is then concentrated under reduced pressure. (E)-1,3-bis(3-ammoniopropyl)-2-((1-methyl-1,2,3,4-tetrahydroquinoxalin-6-yl)diazenyl)-1H-imidazol-3-ium bromide dichloride is obtained as dark powder.

Example 4

In example 4 (E)-1,3-bis(4-ammoniobutyl)-2-((1,4-dipentyl-1,2,3,4-tetrahydroquinoxalin-6-yl)diazenyl)-1H-imidazol-3-ium bromide dichloride is prepared from tetrahydroquinoxaline and 2-aminoimidazole.

Synthesis of 1,4-dipentyl-1,2,3,4-tetrahydroquinoxaline

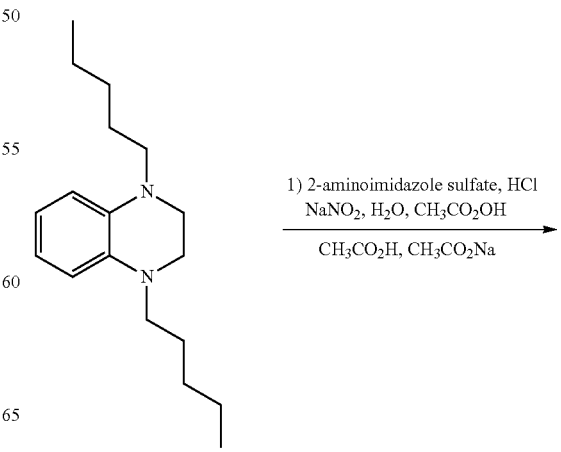

A suspension of tetrahydroquinoxaline (2.68 g), 1-bromopentane (9.06 g) and potassium carbonate (8.28 g) in 20 mL of DMF is stirred at room temperature for 3 days. The resulting mixture is filtered and the filtrate is loaded chromatographed on silica gel to give 1,4-dipentyl-1,2,3,4-tetrahydroquinoxaline (2.2 g) as yellow oil Synthesis of (E)-6-((1H-imidazol-2-yl)diazenyl)-1,4-dipentyl-1,2,3,4-tetrahydroquinoxaline -continued

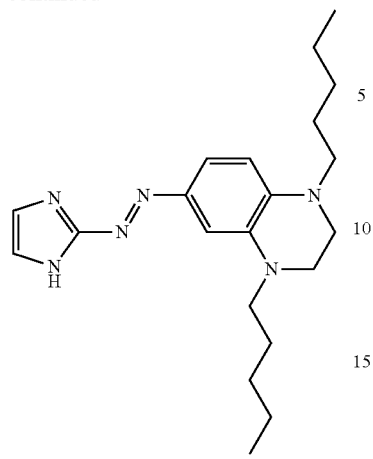

2-Aminoimidazole sulfate (1.53 g) is dissolved in 0.97 mL of concentrated HCl, 1 mL of water, and 3 mL of acetic acid. The resulting solution is cooled to 0° C. A solution of 799 mg in 2 mL of water is added dropwise while the internal temperature is maintained under 5° C. The resulting yellow-brown solution is stirred for 30 minutes at 0° C. In a separate flask equipped with a mechanical stirrer a mixture of 1,4-dipentyl-1,2,3,4-tetrahydroquinoxaline (2.12 g), sodium acetate (1.9 g) and acetic acid (10 mL) is cooled to 0° C. To this slurry is added the diazonium solution slowly while stirring. After the addition is complete, the resulting red suspension is stirred for 1 hour at 0° C. The dark reaction mixture is poured into a large beaker containing 10 g ice. Aqueous NaOH (20%) is added to the suspension slowly until pH 6.5 is reached. The mixture is filtered and sticky dark gum is collected. This crude (E)-6-((1H-imidazol-2-yl)diazenyl)-1,4-dipentyl-1,2,3,4-tetrahydroquinoxaline is purified with column chromatography to give 0.9 g of pure product.

Synthesis of N-(4-bromobutyl)-2,2,2-trifluoroacetamide

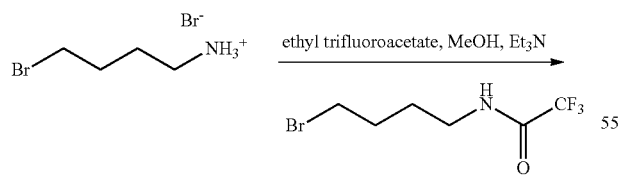

To a mixture of 4-bromo-1-butylamine (9.32 g) and ethyl trifluoroacetate (6.82 g) in 100 mL of methanol at 0° C. is added 6.06 g of trimethylamine dropwise. The reaction solution is warmed to room temperature and stirred overnight. The solvent is evaporated under vacuum and the residue is dissolved in methylene chloride. The solution is washed with water and 1M HCl and concentrated. Crude N-(4-bromobutyl)-2,2,2-trifluoroacetamide is obtained as colorless needles and is used in the next step without further purification.

Synthesis of (E)-2-((1,4-dipentyl-1,2,3,4-tetrahydroquinoxalin-6-yl)diazenyl)-1,3-bis(4-(2,2,2-trifluoroacetamido)butyl)-1H-imidazol-3-ium bromide

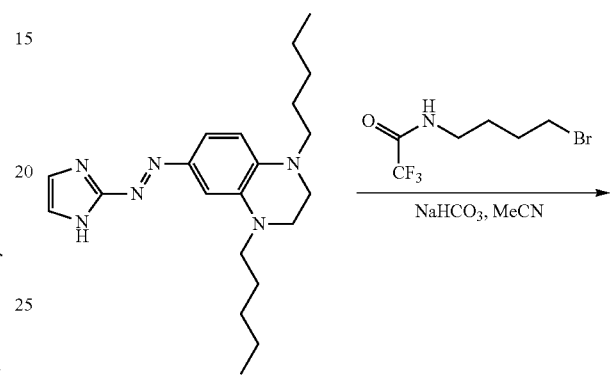

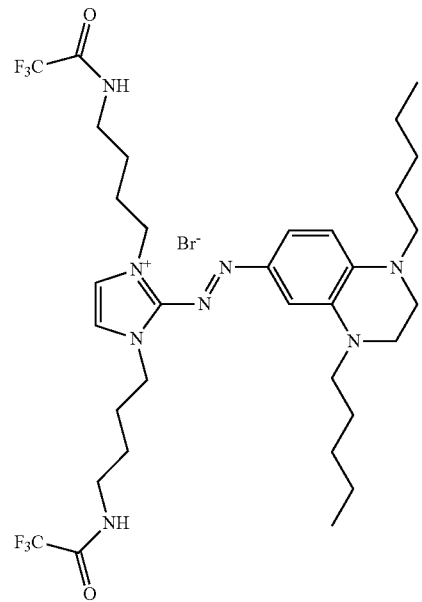

A mixture of crude (E)-6-((1H-imidazol-2-yl)diazenyl)-1,4-dipentyl-1,2,3,4-tetrahydroquinoxaline (630 mg), NaHCO$_3$ (431 mg) and 1.27 g of crude N-(4-bromobutyl)-2,2,2-trifluoroacetamide in 10 mL of MeCN is heated at 86° C. for 20 hours. The reaction is cooled to room temperature and filtered. The filtrate is concentrated and purified by column chromatography. (E)-2-((1,4-dipentyl-1,2,3,4-tetrahydroquinoxalin-6-yl)diazenyl)-1,3-bis(4-(2,2,2-trifluoroacetamido)butyl)-1H-imidazol-3-ium bromide (790 mg) is obtained as dark solid.

Synthesis of (E)-1,3-bis(4-ammoniobutyl)-2-((1,4-dipentyl-1,2,3,4-tetrahydroquinoxalin-6-yl)diazenyl)-1H-imidazol-3-ium bromide dichloride

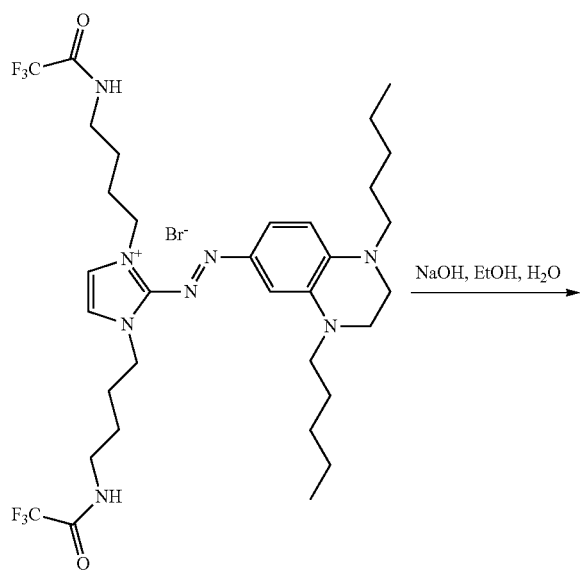

NaOH, EtOH, H₂O (E)-2-((1,4-dipentyl-1,2,3,4-tetrahydroquinoxalin-6-yl)diazenyl)-1,3-bis(4-(2,2,2-trifluoroacetamido)butyl)-1H-imidazol-3-ium bromide (330 mg) is dissolved in 11.3 mL of ethanol and 2.81 mL of 0.5 M sodium hydroxide is added. The mixture is stirred at room temperature for 5 hours. The solution is adjusted to pH 7.0 by adding 1M HCl. The resulting solution is concentrated under vacuum and (E)-1,3-bis(4-ammoniobutyl)-2-((1,4-dipentyl-1,2,3,4-tetrahydroquinoxalin-6-yl)diazenyl)-1H-imidazol-3-ium bromide dichloride is obtained as a dark solid in quantitative yield.

Example 5

In Example 5, (E)-1,3-bis(3-ammoniopropyl)-2-((1-pentyl-1,2,3,4-tetrahydro-quinoxalin-6-yl)diazenyl)-1H-imidazol-3-ium bromide dichloride is prepared from tetrahydroquinoxaline and 2-aminoimidazole.

Synthesis of 1-pentyl-1,2,3,4-tetrahydroquinoxaline

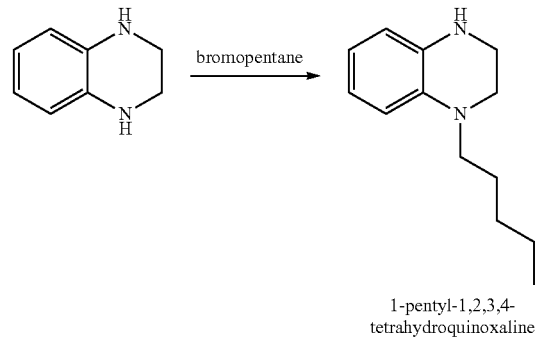

1-pentyl-1,2,3,4-tetrahydroquinoxaline

To a solution of 4.03 g of tetrahydroquinoxaline in 15 mL of DMF is added 4.53 g of 1-bromopentane. The mixture is stirred overnight at room temperature. The reaction mixture is chromatographed on silica gel column to give 1.35 g of pure 1-pentyl-1,2,3,4-tetrahydroquinoxaline.

Synthesis of 2,2,2-trifluoro-1-(4-pentyl-3,4-dihydroquinoxalin-1(2H)-yl)ethan-1-one

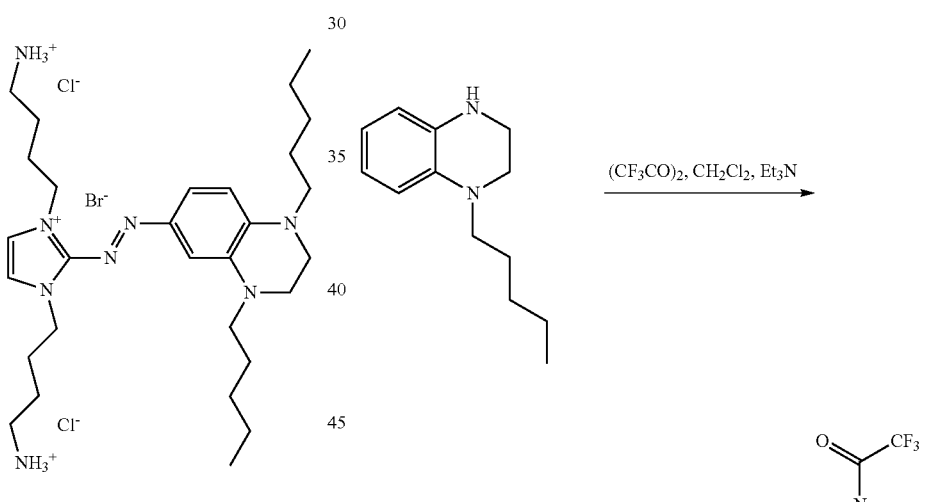

To a mixture of 1.22 g of 1-pentyl-1,2,3,4-tetrahydroquinoxaline and 1.21 g of Et₃N in 10 mL of dichloromethane at 0° C. is added 1.89 g of trifluoroacetic anhydride slowly. The mixture is warmed to room temperature and stirred overnight. Solvent is removed under reduced pressure and the residue is purified with column chromatography to produce 2,2,2-trifluoro-1-(4-pentyl-3,4-dihydroquinoxalin-1(2H)-yl)ethan-1-one as yellow oil (1.3 g).

Synthesis of (E)-1-(7-((1H-imidazol-2-yl)diazenyl)-4-pentyl-3,4-dihydroquinoxalin-1(2H)-yl)-2,2,2-trifluoroethan-1-one

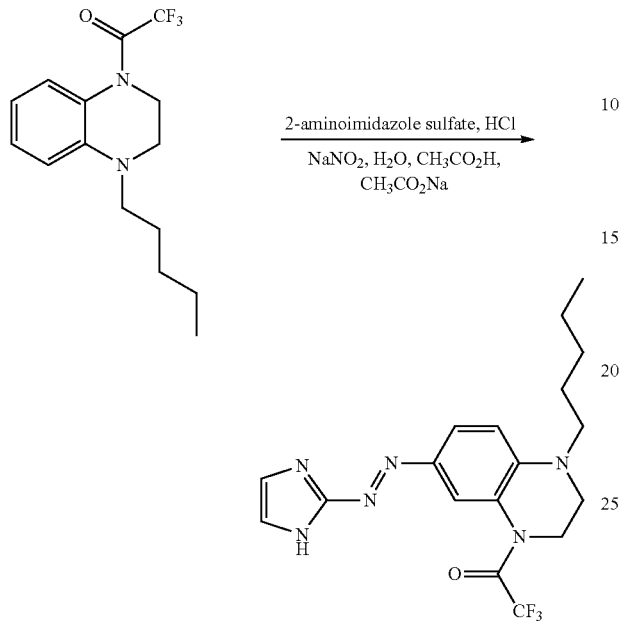

2-Aminoimidazole sulfate (659 mg) is dissolved in 0.42 mL of concentrated HCl, 1 mL of water, and 3 mL of acetic acid. The resulting solution is cooled to 0° C. To the solution is added 345 mg of NaNO₂ in 1 mL of water dropwise so the internal temperature is maintained below 5° C. The resulting yellow-brown solution is stirred for 30 minutes at 0° C. In a separate flask equipped with a mechanical stirrer a mixture of 1.0 g of 2,2,2-trifluoro-1-(4-pentyl-3,4-dihydroquinoxalin-1(2H)-yl)ethan-1-one, 0.82 g of sodium acetate and 3 mL of acetic acid is cooled to 0° C. To this slurry is added the diazonium solution slowly while stirring. After the addition is complete, the resulting red suspension is stirred for 1 hour at 0° C. The dark reaction mixture is poured into a beaker containing 10 g of ice. Aqueous NaOH (20%) is added to the suspension slowly until pH 6.5 is reached. The mixture is filtered and brick red solid is collected. The crude (E)-1-(7-((1H-imidazol-2-yl)diazenyl)-4-pentyl-3,4-dihydroquinoxalin-1(2H)-yl)-2,2,2-trifluoroethan-1-one is dried and used in the next step without further purification (0.94 g).

Synthesis of (E)-2-((1,4-dipentyl-1,2,3,4-tetrahydroquinoxalin-6-yl)diazenyl)-1,3-bis(4-(2,2,2-trifluoroacetamido)butyl)-1H-imidazol-3-ium

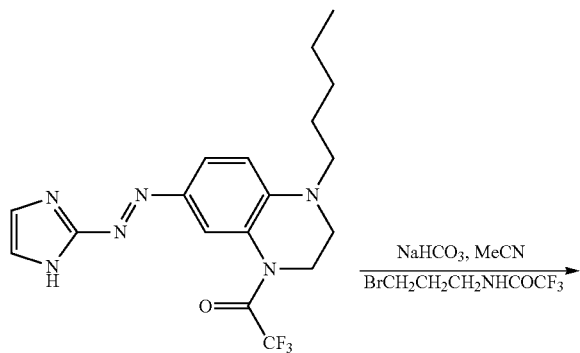

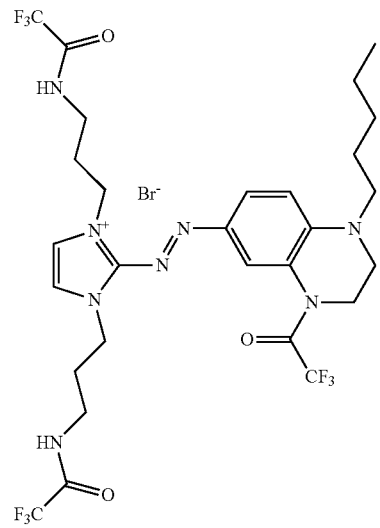

A mixture of 788 mg of (E)-1-(7-((1H-imidazol-2-yl)diazenyl)-4-pentyl-3,4-dihydroquinoxalin-1(2H)-yl)-2,2,2-trifluoroethan-1-one, 504 mg of NaHCO₃ and 1.4 g of N-(4-bromobutyl)-2,2,2-trifluoroacetamide in 12 mL of acetonitrile is heated at 86° C. for 20 hours. The reaction is cooled to room temperature and filtered. The filtrate is concentrated and purified with column chromatography. (E)-2-((1,4-dipentyl-1,2,3,4-tetrahydroquinoxalin-6-yl)diazenyl)-1,3-bis(4-(2,2,2-trifluoroacetamido)butyl)-1H-imidazol-3-ium bromide is obtained as dark red solid (1.1 g).

Synthesis of (E)-1,3-bis(3-ammoniopropyl)-2-((1-pentyl-1,2,3,4-tetrahydroquinoxalin-6-yl)diazenyl)-1H-imidazol-3-ium bromide dichloride

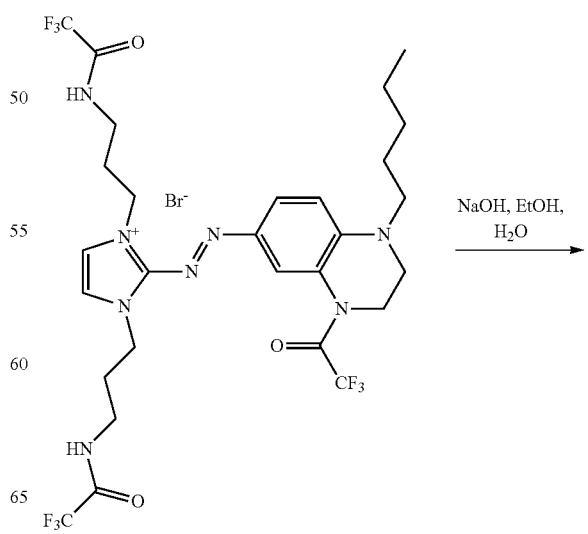

Synthesis of (E)-6-((1H-imidazol-2-yl)diazenyl)-1,4-diallyl-1,2,3,4-tetrahydroquinoxaline

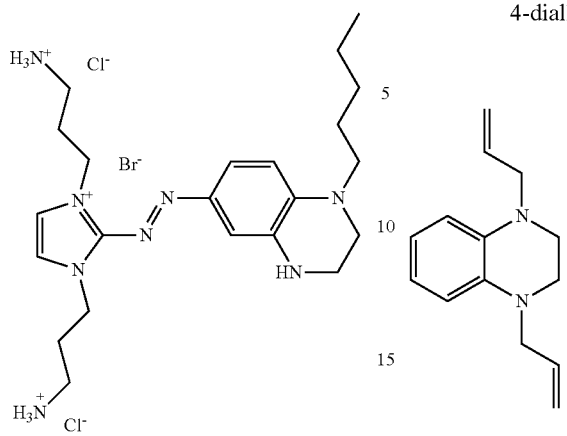

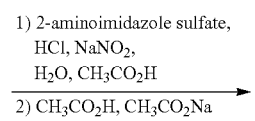

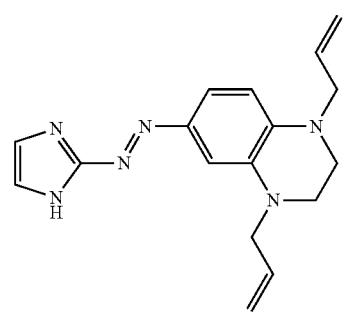

A solution of 781 mg of (E)-2-((1,4-dipentyl-1,2,3,4-tetrahydroquinoxalin-6-yl)diazenyl)-1,3-bis(4-(2,2,2-trifluoroacetamido)butyl)-1H-imidazol-3-ium bromide is stirred in a mixture of 8 mL of 0.5M NaOH and 32 mL of ethanol for 5 hours at room temperature. The resulting blue solution is adjusted to pH 7.0 with 1M aqueous HCl. This solution is concentrated under vacuum to yield (E)-1,3-bis(3-ammoniopropyl)-2-((1-pentyl-1,2,3,4-tetrahydroquinoxalin-6-yl)diazenyl)-1H-imidazol-3-ium bromide dichloride as dark powder (quantitative).

Example 6

In Example 6, (E)-1,3-bis(4-ammoniobutyl)-2-((1,4-diallyl-1,2,3,4-tetrahydroquinoxalin-6-yl)diazenyl)-1H-imidazol-3-ium bromide dichloride is prepared from tetrahydroquinoxaline and 2-aminoimidazole.

Synthesis of 1,4-diallyl-1,2,3,4-tetrahydroquinoxaline

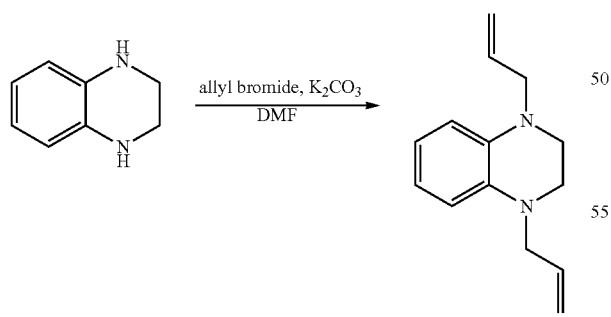

A suspension of 2.68 g of tetrahydroquinoxaline, 7.26 g of allyl bromide and 8.28 g of potassium carbonate in 20 mL DMF is stirred at room temperature for 3 days. The resulting mixture is filtered and the filtrate is chromatographed on silica gel. 1,4-Diallyl-1,2,3,4-tetrahydroquinoxaline is obtained as yellow oil (1.89 g).

2-Aminoimidazole sulfate (1.53 g) is dissolved in 0.97 mL of concentrated HCl, 1 mL of water, and 3 mL of acetic acid. The resulting solution is cooled to 0° C. A solution 799 mg of NaNO$_2$ in 2 mL of water is added dropwise, and the internal temperature is maintained below 5° C. The resulting yellow-brown solution is stirred for 30 minutes at 0° C. In a separate flask equipped with a mechanical stirrer a mixture of 1.65 g of 1,4-diallyl-1,2,3,4-tetrahydroquinoxaline, 1.9 g of sodium acetate and 10 mL of acetic acid is cooled to 0° C. The diazonium solution is added slowly this slurry while stirring. After the addition is complete, the resulting red suspension is stirred for 1 hour at 0° C. The dark reaction mixture is poured into a beaker containing 10 g of ice. Aqueous NaOH (20%) is added to the suspension slowly until pH 6.5 is reached. The mixture is filtered and the dark solid is dried. (E)-6-((1H-imidazol-2-yl)diazenyl)-1,4-diallyl-1,2,3,4-tetrahydroquinoxaline (2.3 g) is used in the next step without further purification.

Synthesis of (E)-2-((1,4-diallyl-1,2,3,4-tetrahydroquinoxalin-6-yl)diazenyl)-1,3-bis(4-(2,2,2-trifluoroacetamido)butyl)-1H-imidazol-3-ium bromide

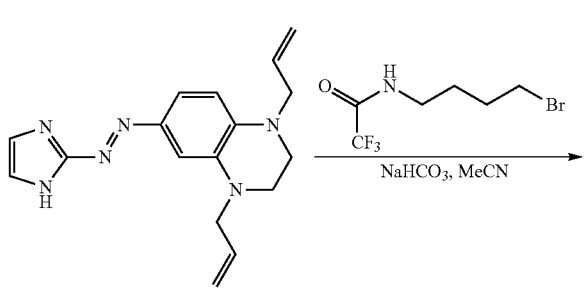

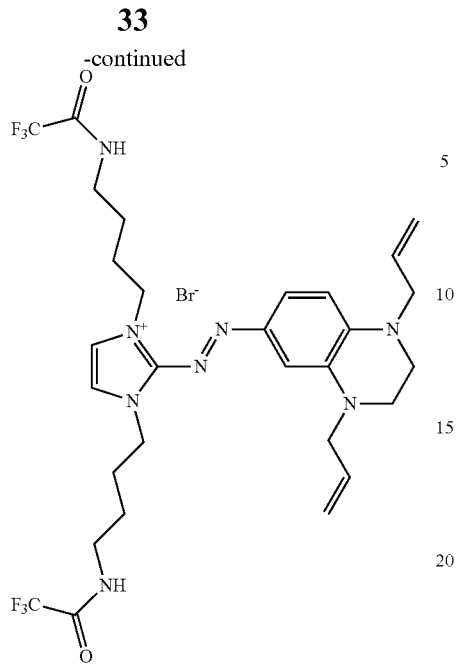

A mixture of 925 mg of (E)-6-((1H-imidazol-2-yl)diazenyl)-1,4-diallyl-1,2,3,4-tetrahydroquinoxaline, 756 mg of NaHCO$_3$ and 2.23 g of N-(4-bromobutyl)-2,2,2-trifluoroacetamide in 15 mL of acetonitrile is heated at 86° C. for 16 hours. The reaction is cooled to room temperature and filtered. The filtrate is concentrated and purified with column chromatography to obtain (E)-2-((1,4-diallyl-1,2,3,4-tetrahydroquinoxalin-6-yl)diazenyl)-1,3-bis(4-(2,2,2-trifluoroacetamido)butyl)-1H-imidazol-3-ium bromide as dark gum (0.85 g).

Synthesis of (E)-1,3-bis(4-ammoniobutyl)-2-((1,4-diallyl-1,2,3,4-tetrahydroquinoxalin-6-yl)diazenyl)-1H-imidazol-3-ium bromide dichloride

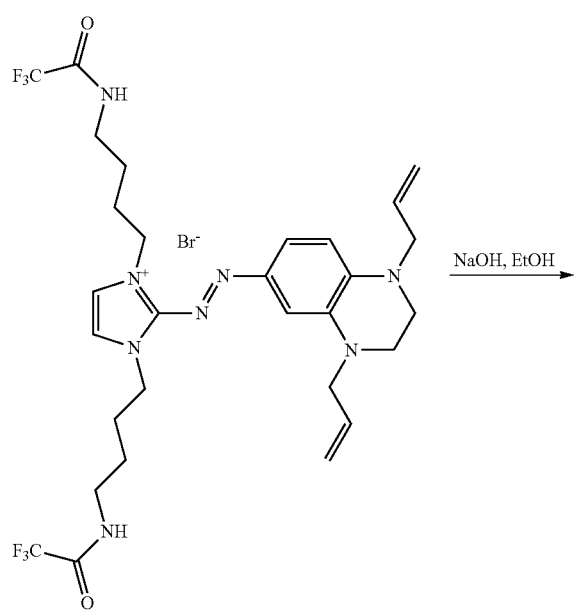

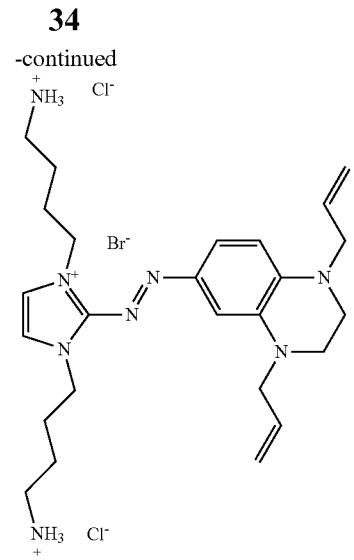

A mixture of (E)-2-((1,4-diallyl-1,2,3,4-tetrahydroquinoxalin-6-yl)diazenyl)-1,3-bis(4-(2,2,2-trifluoroacetamido)butyl)-1H-imidazol-3-ium bromide (450 mg) in 14.93 mL of ethanol and 3.73 mL of 0.5 M NaOH is stirred for 5 hours at room temperature. At completion of the reaction, 1 M HCl is added to lower the solution to pH 7. The solution is concentrated under vacuum and (E)-1,3-bis(4-ammoniobutyl)-2-((1,4-diallyl-1,2,3,4-tetrahydroquinoxalin-6-yl)diazenyl)-1H-imidazol-3-ium bromide dichloride is obtained as a dark material (quantitative).

Example 7

In Example 7, (E)-2-((1,4-diethyl-1,2,3,4-tetrahydroquinoxalin-6-yl)diazenyl)-1,3-dimethyl-1H-imidazol-3-ium methyl sulfate is prepared from quinoxaline and 2-aminoimidazole.

Synthesis of 1,4-diethyl-1,2,3,4-tetrahydroquinoxaline

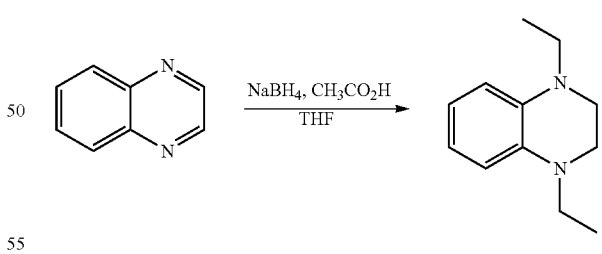

A round bottom flask charged with quinoxaline (1.95 g) and dry 30 mL of THF is cooled to 0° C. To the mixture is added 6 g of sodium borohydride over 15 minutes. The resulting slurry is stirred at 0° C. for 30 minutes and then 27 g of glacial acetic acid is added dropwise over 1 hour. The reaction temperature is maintained at 10° C. for 1 hour and the mixture is heated to reflux. After 16 hours, the reaction mixture is filtered and the filtrate is concentrated under vacuum. The crude 1,4-diethyl-1,2,3,4-tetrahydroquinoxaline is chromatographed on silica gel, dried and 1.55 g is used in the next steps without further purification.

Synthesis of (E)-6-((1H-imidazol-2-yl)diazenyl)-1,4-diethyl-1,2,3,4-tetrahydroquinoxaline

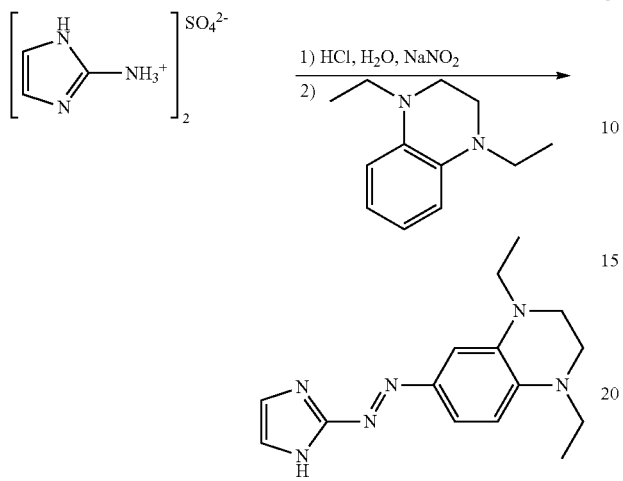

2-Aminoimidazole sulfate (145 mg) is dissolved in 0.34 mL of HCl and 0.4 mL of water and the resulting solution is cooled to 0° C. To the solution is added dropwise 76 mg of NaNO$_2$ in 1 mL of water. The resulting dark brown mixture is stirred for 30 minutes at 0° C. This mixture is then slowly added to a cooled solution of 190 mg of 1,4-diethyl-1,2,3,4-tetrahydroquinoxaline in 1 mL of methanol, keeping the temperature below 5° C. The resulting blue reaction mixture is stirred for 1 hour. Aqueous NaOH is added slowly until the mixture is pH 6.5. The reaction mixture is extracted with ethyl acetate to yield crude (E)-6-((1H-imidazol-2-yl)diazenyl)-1,4-diethyl-1,2,3,4-tetrahydroquinoxaline, which is used in the next step without further purification.

Synthesis of (E)-2-((1,4-diethyl-1,2,3,4-tetrahydroquinoxalin-6-yl)diazenyl)-1,3-dimethyl-1H-imidazol-3-ium methyl sulfate

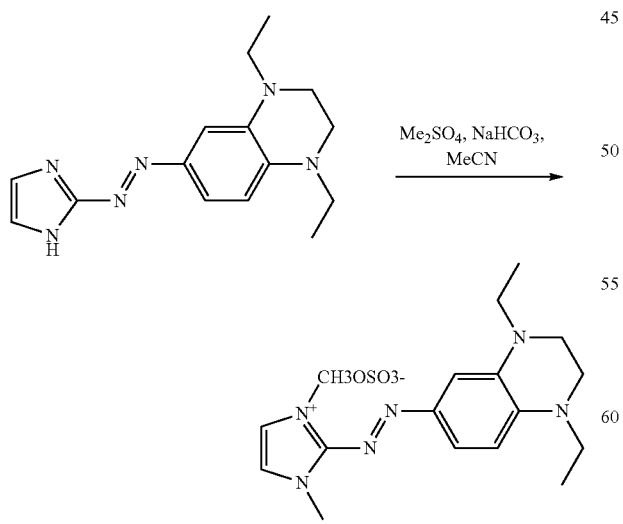

Crude (E)-6-((1H-imidazol-2-yl)diazenyl)-1,4-diethyl-1,2,3,4-tetrahydroquinoxaline is dissolved in 4 of mL dry acetonitrile. NaHCO$_3$ (126 mg) and 378 mg of dimethyl sulfate were added, and the mixture is stirred under reflux for 30 minutes. At completion, the reaction mixture is filtered and concentrated. The residue is purified with silica gel chromatography and (E)-2-((1,4-diethyl-1,2,3,4-tetrahydroquinoxalin-6-yl)diazenyl)-1,3-dimethyl-1H-imidazol-3-ium methyl sulfate is obtained as a blue solid (110 mg).

Example 8

In Example 8, (E)-1,3-dimethyl-2-((2,3,4,5-tetrahydro-1,6-dioxa-3a-azaphenalen-8-yl)diazenyl)-1H-imidazol-3-ium methyl sulfate is prepared from 1,2,3-trifluoro-5-nitrobenzene and diethanolamine Synthesis of 8-nitro-2,3,4,5-tetrahydro-1,6-dioxa-3a-azaphenalene

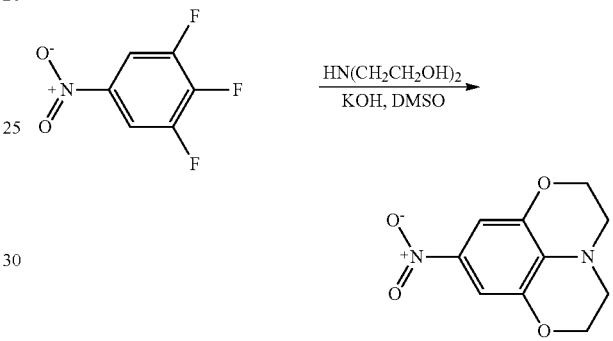

Diethanolamine (7 g) is dissolved in 50 mL of DMSO and 7 g of KOH is added. 3,4,5-Trifluoronitrobenzene (6 g) is added dropwise so that the temperature of the reaction mixture did not exceed 40° C. The reaction is stirred at 40° C. overnight. The mixture is then poured into 500 mL of ice water. The yellow-orange solid (2.1 g) is obtained by filtration is washed with water and dried to give 8-nitro-2,3,4,5-tetrahydro-1,6-dioxa-3a-azaphenalene, which is used in the next step without further purification.

Synthesis of 2,3,4,5-tetrahydro-1,6-dioxa-3a-azaphenalen-8-amine

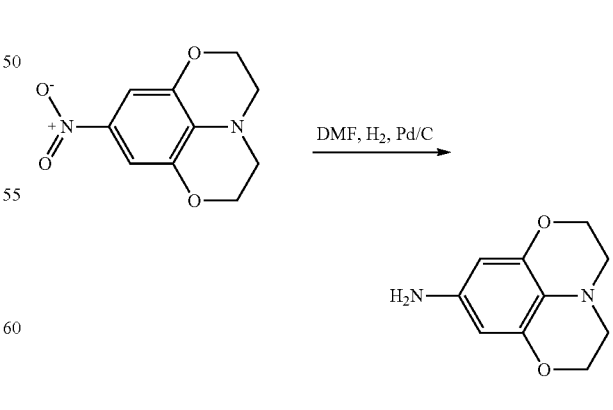

A dried pressure tube containing 111 mg of 8-nitro-2,3,4,5-tetrahydro-1,6-dioxa-3a-azaphenalene, 4 mL of DMF, and 11 mg of Pd/C is charged to 70 psi with hydrogen gas. The mixture is stirred overnight. To the reaction mixture is added 5 mL of 1 M HCl. The resulting solution is filtered and concentrated under vacuum. The 2,3,4,5-tetrahydro-1,6-dioxa-3a-azaphenalen-8-amine obtained is used in the next step without further purification.

Synthesis of (E)-8-((1H-imidazol-2-yl)diazenyl)-2,3,4,5-tetrahydro-1,6-dioxa-3a-azaphenalene

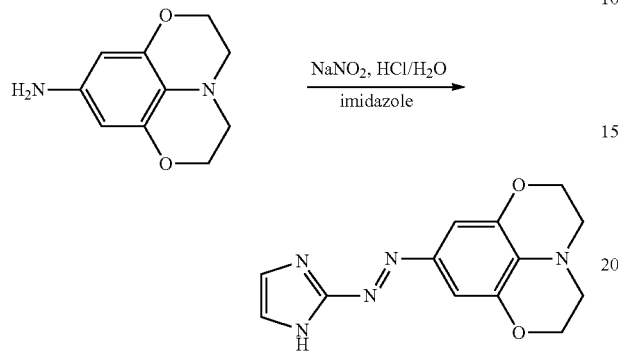

A solution of 96 mg of crude 2,3,4,5-tetrahydro-1,6-dioxa-3a-azaphenalen-8-amine from the previous step in 0.17 mL of concentrated HCl and 0.5 mL of water is cooled to 0° C. in an ice bath. To the mixture is added very slowly a solution of 38 mg of NaNO₂ in 0.5 mL of water while stirring. The reaction is allowed to continue for 30 minutes after complete addition of NaNO₂. Imidazole (37 mg) in 1 mL of water is added to the above solution slowly at 0° C., and the reaction is stirred for 1 hour. Aqueous 10% NaOH solution is added slowly to adjust the reaction to pH 8. The mixture is extracted with ethyl acetate and the organic layers were dried to yield crude (E)-8-((1H-imidazol-2-yl)diazenyl)-2,3,4,5-tetrahydro-1,6-dioxa-3a-azaphenalene, which is used in the next step without further purification.

Synthesis of (E)-1,3-dimethyl-2-((2,3,4,5-tetrahydro-1,6-dioxa-3a-azaphenalen-8-yl)diazenyl)-1H-imidazol-3-ium methyl sulfate

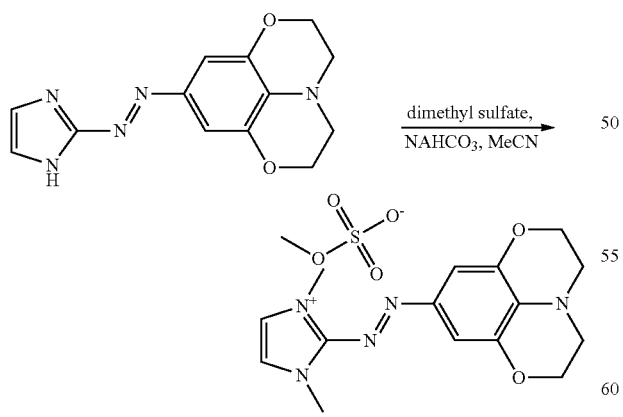

A solution of 135 mg of crude (E)-8-((1H-imidazol-2-yl)diazenyl)-2,3,4,5-tetrahydro-1,6-dioxa-3a-azaphenalene, 126 mg of NaHCO₃, and 142 mg of dimethyl sulfate in 5 mL of acetonitrile is heated under reflux for 4 hours. The reaction mixture is cooled to room temperature and filtered. The filtrate is concentrated under reduced pressure and the residue obtained is purified with column chromatography to produce (E)-1,3-dimethyl-2-((2,3,4,5-tetrahydro-1,6-dioxa-3a-azaphenalen-8-yl)diazenyl)-1H-imidazol-3-ium methyl sulfate as a dark solid (43 mg).

Example 9

In Example 9, (E)-1,3-bis(4-ammoniobutyl)-2-((1,4-diallyl-1,2,3,4-tetrahydroquinoxalin-6-yl)diazenyl)-1H-imidazol-3-ium bromide dichloride is prepared from tetrahydroquinoxaline and 2-aminoimidazole.

Synthesis of (E)-2-((1,4-diethyl-1,2,3,4-tetrahydroquinoxalin-6-yl)diazenyl)-1,3-bis(4-(2,2,2-trifluoroacetamido)butyl)-1H-imidazol-3-ium bromide

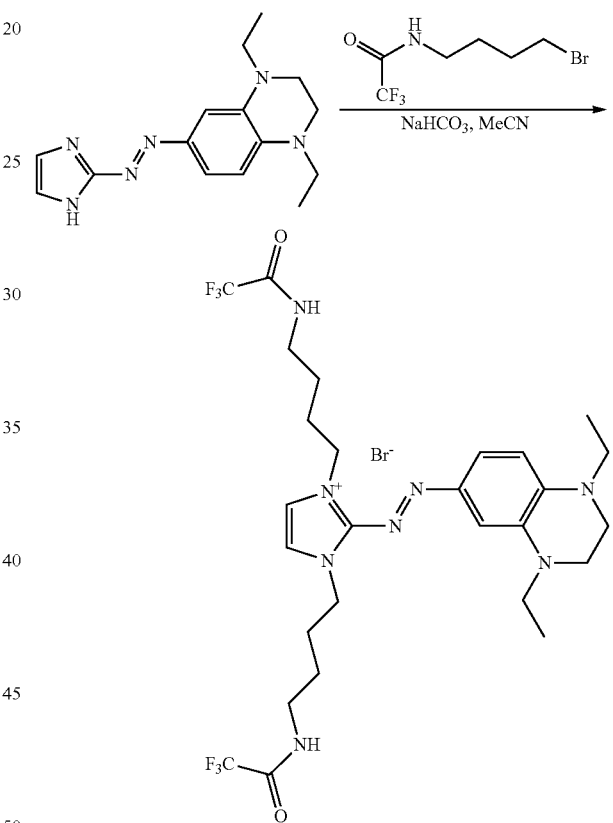

A mixture of 4-butylpropylamine trifluoroacetamide (20.00 g, 80.65 mmol), (E)-6-((1H-imidazol-2-yl)diazenyl)-1,4-diethyl-1,2,3,4-tetrahydroquinoxaline (7.50 g, 26.37 mmol) and NaHCO3 (4.90 g, 58.33 mmol) in acetonitrile (300 mL) is stirred at reflux under argon for 18 hours. After cooling to room temperature, additional NaHCO3 (500 mg, 5.95 mmol) and 2 (2.00 g, 8.06 mmol) were added. The reaction is stirred at reflux for 20 hours. The reaction mixture is cooled to room temperature, concentrated, and then purified by silica gel chromatography. The appropriate fractions were combined, concentrated and dried in vacuo at 40° C. The solids were washed with hexanes (2×50 mL) and re-dried in vacuo at 40° C. to give (E)-2-((1,4-diethyl-1,2,3,4-tetrahydroquinoxalin-6-yl)diazenyl)-1,3-bis(4-(2,2,2-trifluoroacetamido)butyl)-1H-imidazol-3-ium bromide as a dark blue film (12.3 g, 66.6% yield).

Synthesis of (E)-2-((1,4-diethyl-1,2,3,4-tetrahydro-quinoxalin-6-yl)diazenyl)-1,3-bis(4-(2,2,2-trifluoro-acetamido)butyl)-1H-imidazol-3-ium bromide

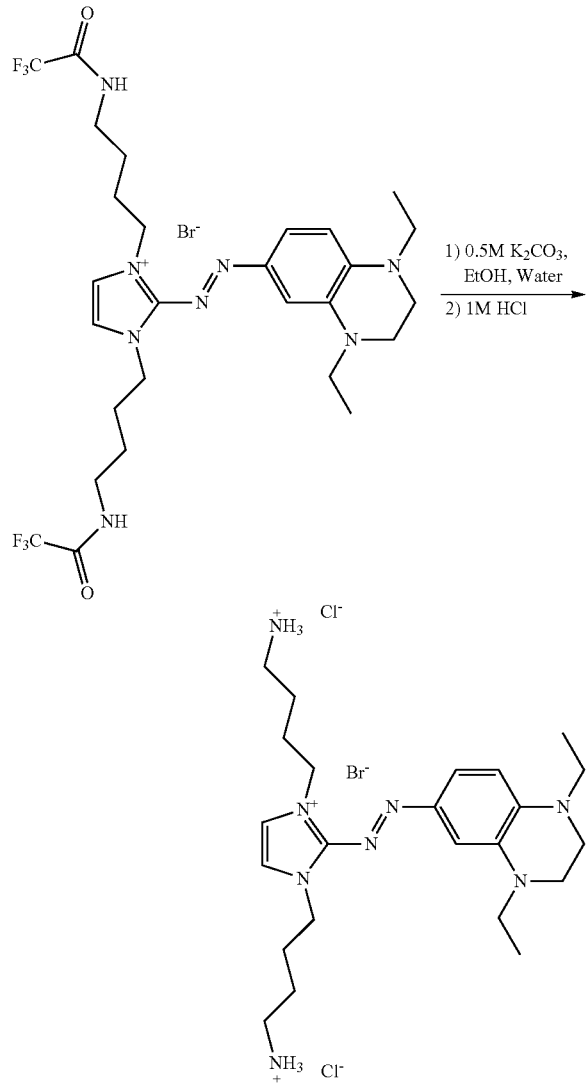

To a solution of (E)-2-((1,4-diethyl-1,2,3,4-tetrahydroquinoxalin-6-yl)diazenyl)-1,3-bis(4-(2,2,2-trifluoroacetamido)butyl)-1H-imidazol-3-ium bromide (505 mg, 0.722 mmol) in ethanol (24 mL) is added an aqueous solution of $K_2CO_3$ (400 mg, 2.89 mmol in 6 mL H2O). The reaction mixture is heated at 40° C. for 20 hours, cooled to RT, additional aqueous $K_2CO_3$ (100 mg, 0.72 mmol in 1 mL $H_2O$) is added. The reaction mixture is heated at 40° C. for 6 hours, cooled to room temperature and additional aq. $K_2CO_3$ (100 mg, 0.72 mmol in 1 mL $H_2O$) is added. The reaction mixture is heated at 40° C. for 16 hours, cooled to room temperature and carefully neutralized to pH 7.0 using 1N HCl (progress followed with a pH meter). Ethanol is removed in vacuo, and the residue is dissolved in water (25 mL). The aqueous solution of (E)-2-((1,4-diethyl-1,2,3,4-tetrahydroquinoxalin-6-yl)diazenyl)-1,3-bis(4-(2,2,2-trifluoroacetamido)butyl)-1H-imidazol-3-ium bromide is washed with $CH_2Cl_2$ (5×50 mL) then the water is removed in vacuo to give solid (E)-2-((1,4-diethyl-1,2,3,4-tetrahydroquinoxalin-6-yl)diazenyl)-1,3-bis(4-(2,2,2-trifluoroacetamido)butyl)-1H-imidazol-3-ium bromide.

Exemplary Formulations

| | % by weight |
|---|---|
| Composition A | |
| Direct Dye[1] | 0.01-2.5 |
| Ammonium Hydroxide (aq. 28% active) | 4.50 |
| Water | q.s. to 100 |
| Composition B | |
| Direct Dye[1] | 0.01-2.5 |
| Ammonium carbonate | 10.00 |
| Water | q.s. to 100 |
| Composition C | |
| Direct Dye[1] | 0.01-2.5 |
| FlexiThix ™[3] | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition D | |
| Direct Dye[1] | 0.01-2.5 |
| Aculyn ™ 46[4] | 15.80 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition E | |
| Direct Dye[1] | 0.01-2.5 |
| Plantaren ® 2000 N UP[2] | 20.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition F | |
| Direct Dye[1] | 0.01-2.5 |
| Non-anionic foaming agent | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |

[1]: The direct dye may be any one of the direct dyes described herein
[2]: Chemical makeup supplied by BASF
[3]: PVP polymer supplied by Ashland
[4]: PEG-150/Stearyl/SMDI copolymer supplied by Rohm and Haas The hair color compositions described herein may be formed as thick liquid, cream, gel, emulsion, foam, aerosol mousse or as a solid form to which water is added to generate the oxidant and form a thickened vehicle suitable for hair coloring. They may comprise in addition to the ingredients indicated above further ingredients in order to further enhance the properties of the composition, including but not limited to: solvents; oxidative dyes, direct dyes; oxidizing agents; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein compounds, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A few of these ingredients are discussed hereinbelow, whose disclosure is of course non-exhaustive.

Optional Ingredients

The hair color compositions described herein may comprise, in addition to the ingredients indicated above, optional ingredients in order to further enhance the properties of the composition.

Suitable optional ingredients include, but are not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof. Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.
Solvents The hair color compositions described herein may further comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In an embodiment, the solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least about 50%, alternatively from at least about 60%, alternatively from at least about 70%, by weight of the total composition. In an embodiment, the composition may comprise a total amount of organic solvents ranging from about 1% to about 30%, by weight of the total hair color composition.

Oxidizing Agent

The hair color composition described herein may comprise at least one source of an oxidizing agent. Preferred oxidizing agents for use herein are water soluble peroxygen oxidizing agents. Water-soluble peroxygen oxidizing agents are well known in the art and include, but are not limited to, hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidases, and uricases and their substrates may also be used. Mixtures of two or more such oxidizing agents can also be used if desired. The oxidizing agents may be provided in aqueous solution or as a powder which is dissolved prior to use. In an embodiment, the oxidizing agents may be selected from the group consisting of hydrogen peroxide, percarbonate, persulfates and combinations thereof.

In an embodiment, the hair color composition may comprise from 0.1% to 20% by weight, or from 1% to 15% by weight, or from 2% to 10% by weight of the oxidizing agent.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

The oxidizing agent may comprise from 0.1% to 15% by weight, or from 1% to 10% by weight, or from 1% to 8% by weight of a hydrogen carbonate ion; and from 0.1% to 10% by weight, or from 1% to 7% by weight, or from 2% to 5% by weight of the oxidizing agent of a source of hydrogen peroxide.

Alkalizing Agent

The hair color composition described herein may further comprise an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. In an embodiment, the alkalizing agent may be ammonia and/or monoethanolamine.

The hair color compositions described herein may comprise from about 0.1% to about 10%, preferably from about 0.5% to about 6%, more preferably from about 1% to about 4% by weight of the alkalizing agent relative to the total weight of the composition.

The hair colorant compositions described above may have a pH of from 7 to 12, alternatively from 8 to 11. For embodiments comprising a peroxymonocarbonate ion, the pH may be up to and including pH 9.5, alternatively from 7.5 to 9.5, alternatively from 8.4 to 9.5, alternatively from 8.5 to 9.4, alternatively 9.0, and alternatively 9.3.

Any sub-components of the hair color compositions, such as a tint composition or an oxidizing composition, may have a different pH from the hair colorant composition. For example, if the tint composition comprises an alkalizing agent, the tint composition will have an alkaline pH, such as higher than 7. In an embodiment, the oxidizing composition may comprise an acidic pH of less than 7.

When the hair color composition described herein is obtained by mixing a developer and a tint composition prior to use, the alkalizing agent is generally present in the tint composition.

Oxidative Dye Precursors

In addition to the direct dye compounds described herein, the hair color composition may further comprise one or more oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

In an embodiment, the hair color composition may comprise a total amount of oxidative dye precursors ranging up to about 12%, alternatively from about 0.1% to about 10%, alternatively from about 0.3% to about 8%, alternatively from about 0.5% to about 6%, by weight of the total composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, (2,3-diamino-6,7-dihydro-1H,5H-pyrazolo[1,2-a]pyrazol-1-one dimethanesulfonate), 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the hair color composition described herein is obtained by mixing a tint composition and a developer composition, the primary intermediates and couplers may be incorporated into the tint composition.

Additional Direct Dyes

The hair color composition may further comprise additional compatible direct dyes, in an amount sufficient to provide additional coloring, particularly with regard to intensity. In an embodiment, the composition may comprise a total amount of direct dyes ranging from about 0.05% to about 4%, by weight of the total composition.

Suitable direct dyes include but are not limited to: HC Yellow 17, HC Blue 18, HC Yellow 16, HC Red 18, Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the hair color composition is obtained by mixing a tint composition and a developer composition, the additional direct dyes may be incorporated into the tint composition.

Chelants

The hair color composition described herein may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & RD Hancock, Metal Complexes in Aqueous Solution, Plenum Press, New York & London (1996), both incorporated herein by reference.

In an embodiment, the hair color composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof. Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO3H2) or its derivative—PO3R2, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, the composition comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the hair color composition is obtained by mixing a tint composition and a developer composition, the chelants may be incorporated in the tint composition and/or in the developer composition. A chelant may be present in the developer composition for stability.

Radical Scavengers

The hair color compositions described herein may comprise a radical scavenger. As used herein the term radical scavenger refers to a species that can react with a radical, to convert the radical species by a series of fast reactions to an unreactive or less reactive species. The radical scavenger is also preferably selected such that it is not an identical species as the alkalising agent and is present in an amount sufficient to reduce the damage to the hair during the colouring/bleaching process. The compositions of the present invention comprise a radical scavenger from about 0.1% to about 10%, preferably from about 1% to about 7% by weight of the radical scavenger relative to the total weight of the composition.

Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methyl pyrazol-5-one-3-carboxylate, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. In some embodiments, the inventive compositions may comprise glycine, sarcosine, lysine, serine, 2-methoxyethylamine, glucosamine, glutamic acid, morpholine, piperidine, ethylamine, 3-amino-1-propanol, or mixtures thereof.

pH Modifiers and Buffering Agents

The hair color compositions described herein may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The hair color compositions described herein may further comprise a thickener in an amount sufficient to provide the composition with a viscosity so that it can be readily applied to the hair without unduly dripping off the hair and causing mess.

In an embodiment, the hair color compositions may comprise a total amount of thickeners ranging from at least about 0.1%, alternatively at least about 1%, alternatively at least about 10%, alternatively at least about 20%, by weight of the total composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof. Commercially available anionic materials include those sold as Sepigel 305 by Seppic.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (XV) below

$$CH_2=C(R_1)CH_2OB_nR \quad\quad\quad (XV)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (XVI) below

$$CH_2=C(R_1)COOH \quad\quad\quad (XVI)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (XVII) below

$$CH_2=C(R_1)COOB_nR_2 \quad\quad\quad (XVII)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (XVIII) below

   (XVIII)

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

In an embodiment, the associative polymers may comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculyn-22 by Rohm & Haas; Permulen TR1, Carbopol 2020, Carbopol Ultrez-21/-30 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/1382/2984/5984 by Noveon, Synthalen M/Synthalen L/Synthalen K/Synthalen CR by 3V, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglycans, gum arabics, gum tragacanths, ghatti gums, karaya gums, carob gums, galactomannans, such as guar gums, and non-ionic derivatives thereof (hydroxypropyl guar) and biopolysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie Another preferred polysaccharide is hydroxypropyl starch derivative, particularly hydroxypropyl starch phosphate, commercially available as Structure XL® by National Starch, a hydrophobically modified cellulose derivative, commercially available as Structure® Cel 500 HM by AkzoNobel.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), polyvinylpyrrolidone (Povidone, FlexiThix™), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Dicetyl phosphate and Cetearyl alcohol (available as Crodafos CES), and mixtures thereof.

Salt

In an embodiment, cosmetically acceptable salt, such as ammonium, sodium or potassium salts with appropriate counter ions, may be added to the hair color compositions described herein to act as leveling agents to minimize patchy coloring results.

Carbonate Ion Sources

The hair color compositions described herein may further comprise a source of carbonate ions, carbamate ions, hydrogen carbonate ions, and mixtures thereof in a sufficient amount to reduce damage to the hair during the coloring process.

In an embodiment, the hair color compositions may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The hair color compositions described herein may further comprise a conditioning agent, and/or be used in combination with a composition comprising a conditioning agent.

In an embodiment, the hair color compositions may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials may be cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane (Si(CH$_3$)$_2$—O) units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be (CH$_3$)$_3$Si—O, R$_{12}$(CH$_3$)$_2$Si—O, where R$_{12}$ can be either OH or OR$_{13}$, where R$_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about 5×10$^6$, alternatively from about 1000 to about 3×10$^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinylpyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); coplolymers of vinyl pyrrolidone and dialkyaminoalkyl acrylates or methactylates, including polymers known as Polquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—N+(R1)(R2)-A1-N+(R3)(R4)-B1-] [2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X—] in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0, t=0, R6, R7, R8 and R9 are methyl groups, and A is —CH2-CH2-O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12 (CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In an embodiment, the cationic polymer is selected from the group consisting of polyquaternium 37, polyquaternium 7, polyquaternium 22, polyquaternium 87, and mixtures thereof; alternatively from the group consisting of polyquaternium 37, polyquaternium 22, and mixtures thereof.

Surfactants

The hair color compositions described herein may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

In an embodiment, the hair color compositions may comprise a total amount of surfactants ranging from about 0.01% to about 60%, alternatively from about 0.05% to about 30%, alternatively from about 0.1% to about 25%, alternatively from about 0.1% to about 20%, by weight of the total composition.

The compositions may comprise a mixture of an anionic surfactant and an amphoteric surfactant with one or more nonionic surfactants. The composition may comprise a total amount of anionic surfactant ranging from about 0.01% to about 20%, alternatively from about 0.05% to about 15%, alternatively from about 0.1% to about 15%, by weight of the total composition; and a total amount of amphoteric and/or nonionic components, which may range independently from each other from about 0.01% to about 15%, alternatively from about 0.05% to about 10%, alternatively from about 0.1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. No. 2,781,354 and having the structures of: $R_2$—CON HCH$_2$CH$_2$—N$^+$($R_3$)($R_4$)(CH$_2$COO$^-$), (XIX) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—CONHCH$_2$CH$_2$—N(B)(C) (XX) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (XXI) below:

(XXI)

wherein $X^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from ($C_{12}$-$C_{22}$)alkylamido($C_2$-$C_6$)alkyl and ($C_{12}$-$C_{22}$) alkylacetate radicals. A suitable cationic surfactant is, for example, a dicetyldimethyl ammonium salt (for example chloride);

B) Quaternary ammonium salts of imidazolinium of formula (XXII) below:

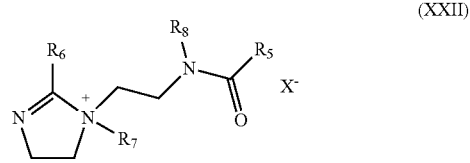

(XXII)

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (XXIII):

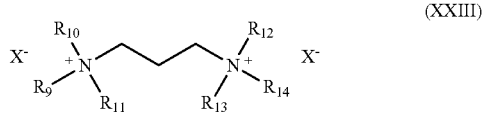

(XXIII)

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammonium dichloride.

D) Quaternary ammonium salts comprising at least one ester function, of formula (XXIV) below:

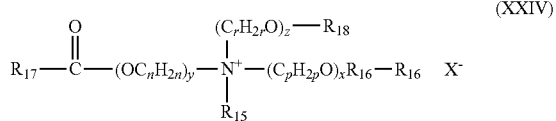

(XXIV)

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X— is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XXXXI) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

Data

Uptake and washfastness: The uptake total color change ($\Delta E^1$) describes how much the hair color has changed after white Piedmont hair strands supplied by International Hair Importers & Products has been dyed. $\Delta E$ is calculated as the square root of sum of squares of $\Delta L^*$, $\Delta a^*$ and $\Delta b^*$. The total color change for washfastness ($\Delta E^2$) is measured after the dyed hair switches are processed through a 12-cycle rinse study. One cycle is defined as two shampoo treatments followed by a conditioning treatment. The hair switches are blow dried between each shampoo treatment. Color data is collected after the hair is properly dried on a Minolta spectrophotometer CM-3700d. Example A is a control example and is commercially available. Examples B through J are embodiments of the washfast direct dye compounds described herein.

TABLE 1

Colorstrike and washfastness data on natural white hair from imidazolium azo dyes.

| | Structure | $\Delta E^1$ | $\Delta E^2$ |
|---|---|---|---|
| A | 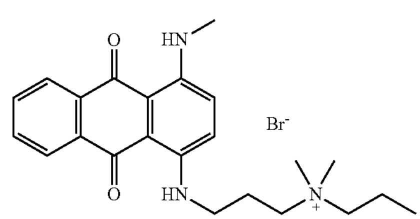 | 76 | 17 |
| B | 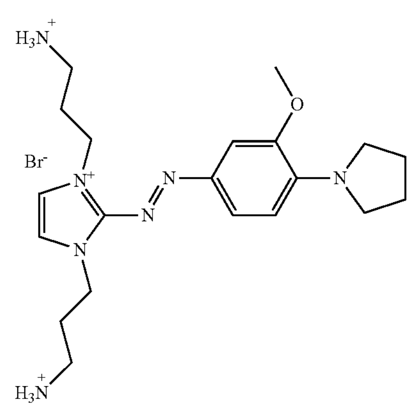 [SMILES: [Br-] ; COc1cc(/N=N/c2n(CCCN)cc[n+]2CCCN)ccc1N1CCCC1] | 70.33 | 7.65 |
| C | 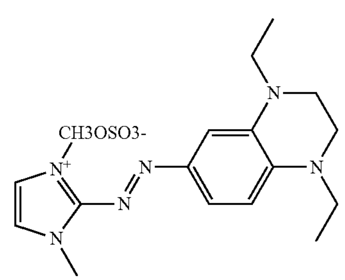 | 64.42 | 7.75 |

TABLE 1-continued
Colorstrike and washfastness data on
natural white hair from imidazolium azo dyes.
| Structure | ΔE¹ | ΔE² |
|---|---|---|
| D | 63.63 | 5.58 |
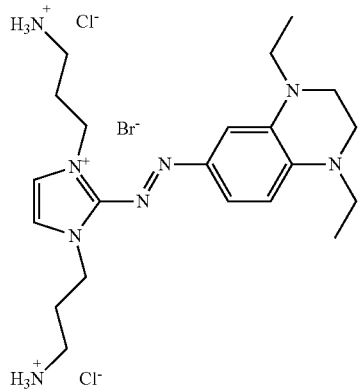 [SMILES: CCN1CCN(CC)c2cc(/N=N/c3n(CCCN)cc[n+]3CCCN)ccc21 ; [Cl-] ; [Br-] ; [Cl-]]
| E | 64.18 | 4.09 |
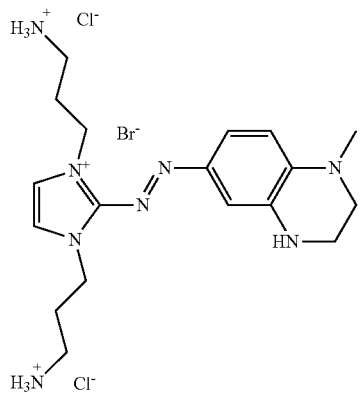 [SMILES: [Cl-] ; CN1CCNc2cc(/N=N/c3n(CCCN)cc[n+]3CCCN)ccc21 ; [Br-] ; [Cl-]]
| F | 63.74 | 4.78 |
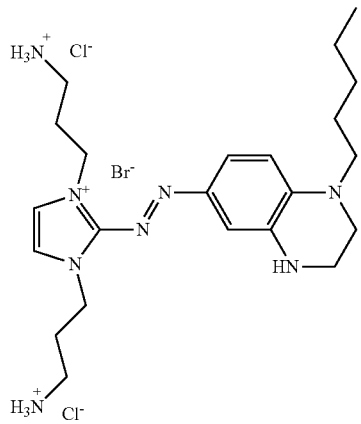 [SMILES: CCCCCN1CCNc2cc(/N=N/c3n(CCCN)cc[n+]3CCCN)ccc21 ; [Cl-] ; [Br-] ; [Cl-]]
TABLE 1-continued
Colorstrike and washfastness data on
natural white hair from imidazolium azo dyes.
| Structure | ΔE¹ | ΔE² |
|---|---|---|
| G | 62.04 | 9.16 |
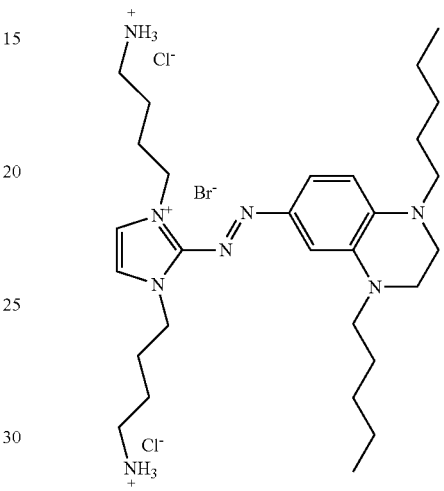
| H | 62.73 | 7.12 |
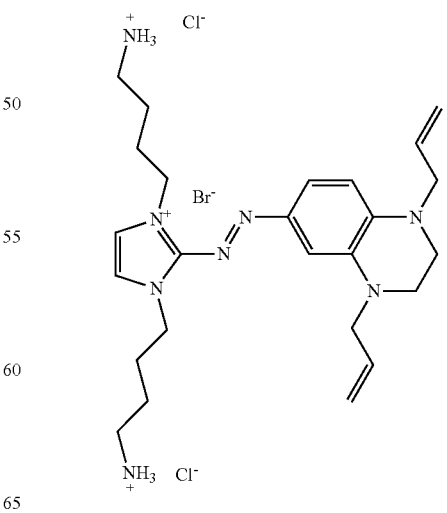

TABLE 1-continued

Colorstrike and washfastness data on
natural white hair from imidazolium azo dyes.

| Structure | $\Delta E^1$ | $\Delta E^2$ |
|---|---|---|
| I 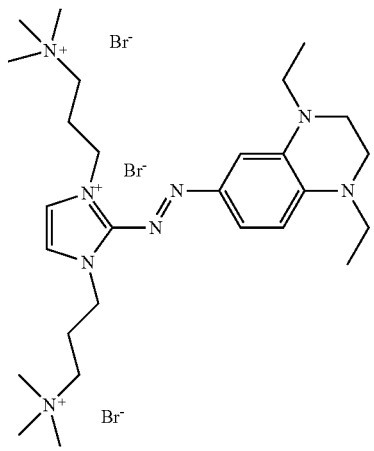 | 62.42 | 6.03 |
| 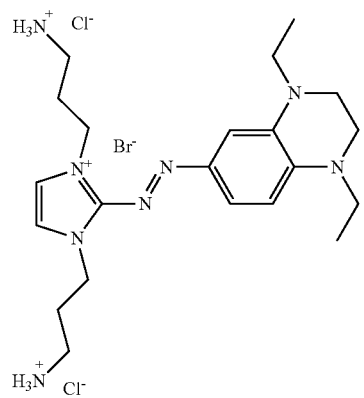 | 60.07 | 3.81 |

[1] uptake on natural white virgin hair from water adjusted to pH 10.8 with 28% ammonia, and this solution is mixed with an equal volume of a 6% commercial hydrogen peroxide solution, such as Clairol Professional ® Soy 4Plex Clairoxide ®.

TABLE 2

On-tone fading data on virgin natural white hair after 24 shampoos, measured as change in hue angle, for a shade made from blue direct dye (E)-1,3-bis(3-ammoniopropyl)-2-((1,4-diethyl-1,2,3,4-tetrahydroquinoxalin-6-yl)diazenyl)-1H-imidazol-3-ium bromide dichloride) and a yellow direct dye of complementary structure ((E)-2-((5-amino-1-hexyl-1H-pyrazol-4-yl)diazenyl)-1,3-bis(3-aminopropyl)-1H-imidazol-3-ium bromide dihydrochloride).

| Compound | Structures | Hair Type | Δh after a 12-cycle rinse - blonde virgin hair |
|---|---|---|---|
| (E)-1,3-bis(3-ammoniopropyl)-2-((1,4-diethyl-1,2,3,4-tetrahydroquinoxalin-6-yl)diazenyl)-1H-imidazol-3-ium bromide dichloride | equimolar | Virgin Natural White | −6.80 |

+

TABLE 2-continued

On-tone fading data on virgin natural white hair after 24 shampoos, measured as change in hue angle, for a shade made from blue direct dye (E)-1,3-bis(3-ammoniopropyl)-2-((1,4-diethyl-1,2,3,4-tetrahydroquinoxalin-6-yl)diazenyl)-1H-imidazol-3-ium bromide dichloride) and a yellow direct dye of complementary structure ((E)-2-((5-amino-1-hexyl-1H-pyrazol-4-yl)diazenyl)-1,3-bis(3-aminopropyl)-1H-imidazol-3-ium bromide dihydrochloride).

| Compound | Structures | Hair Type | Δh after a 12-cycle rinse - blonde virgin hair |
|---|---|---|---|
| (E)-2-((5-amino-1-hexyl-1H-pyrazol-4-yl)diazenyl)-1,3-bis(3-aminopropyl)-1H-imidazol-3-ium bromide dihydrochloride | [structure] | Bleached Yak | −3.96 |

Smaller the hue angle change (Δh) = better on-tone fading.
[2]washfastness on natural white virgin hair using a commercial SLS shampoo.

The smaller the total color change ($\Delta E^2$) for washfastness after 24 shampoos, the more washfast the dye is. Notably, examples B through J, embodiments of the washfast direct dyes described herein, exhibited superior washfastness to example A, a commercially available direct dye compound known in the art.

It is noted that terms like "preferably," "usually", "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of dyeing the hair, the method comprising:
  a. applying to the hair a hair color composition comprising one or more direct dye compounds, the one or more direct dye compounds each comprising:
    i. a blue-violet or blue chromophore;
    ii. one or two permanent cations, wherein the permanent cations are pendant to the chromophore or part of the chromophore, and wherein the chromophore and the permanent cations form a core structure; and
    iii. one to four incipient cations, wherein each of the one to four incipient cations is pendant via a linker group to the core structure, and wherein the incipient cations are neutral,
    iv. one or more C2-C9 hydrophobic moieties, wherein the one or more C2-C9 hydrophobic moieties are pendant to the core structure;
  wherein the one or more direct dye compounds enter the hair shaft after the hair color composition is applied to the hair; and
  wherein the hair color composition has a pH of from about 6 to about 11;

b. rinsing the hair with water;
wherein the pH of the hair after rinsing is from about 3.5 to about 6; and
wherein the rinsing of the hair causes one or more of the one to four incipient cations to change from neutral to positively charged inside of the hair shaft,
wherein the chromophore has a structure according to Formula (X), or a tautomer or salt thereof,

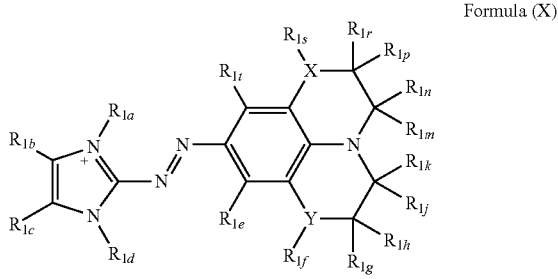

Formula (X)

wherein
(i) $R_{1g}$, $R_{1h}$, $R_{1j}$, $R_{1k}$, $R_{1m}$, $R_{1n}$, $R_{1p}$ and $R_{1r}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, nitro, nitroso, cyano, a heterocyclic moiety, thioether, thiol with or without a linker group, alkylsulfonate, alkylsulfate, carboxylalkyl, acrylamide or substituted acrylamides with or without a linker group, vinylsulfone with or without a linker group, sulfonyl ethyl sulfate with or without a linker group, halo-s-triazines with or without a linker group, halopyrimidines with or without a linker group, or haloquinoxalines with or without a linker group;
(ii) $R_{1b}$, $R_{1c}$, $R_{1e}$ and $R_{1t}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, or haloquinoxalines with a linker group;
(iii) $R_{1f}$ and $R_{1s}$ are each independently hydrogen, alkyl, halogen substituted alkyl, alkenyl, alkynyl, aryl, hydroxyalkyl, aminoalkyl, alkyl group carrying a quaternary ammonium cation, acyl, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, or haloquinoxalines with a linker group;
(iv) $R_{1a}$ and $R_{1d}$ are each independently alkyl, halogen substituted alkyl, alkenyl, alkynyl, aryl, hydroxyalkyl, aminoalkyl, alkyl group carrying a quaternary ammonium cation, alkyl group carrying a quaternary ammonium cation, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, or haloquinoxalines with a linker group; and
(v) X and Y are each independently an oxygen or a nitrogen atom; wherein in the case where X and/or Y is oxygen atom, the corresponding group attached to the oxygen atom, $R_{1f}$ and/or $R_{1s}$, ceases to exist.

2. The method of claim 1, wherein at least one of X and Y is an oxygen atom.

3. The method of claim 1, wherein the hair color composition further comprises from about 0.1% to about 20%, by weight of the composition, of at least one oxidizing agent.

4. A method of dyeing the hair, the method comprising:
a. applying to the hair a hair color composition comprising one or more direct dye compounds, the one or more direct dye compounds each comprising:
   i. a blue-violet or blue chromophore;
   ii. one or two permanent cations, wherein the permanent cations are pendant to the chromophore or part of the chromophore, and wherein the chromophore and the permanent cations form a core structure; and
   iii. one to four incipient cations, wherein each of the one to four incipient cations is pendant via a linker group to the core structure, and wherein the incipient cations are neutral;
   iv. one or more C2-C9 hydrophobic moieties, wherein the one or more C2-C9 hydrophobic moieties are pendant to the core structure;
wherein the one or more direct dye compounds enter the hair shaft after the hair color composition is applied to the hair; and
wherein the hair color composition has a pH of from about 6 to about 11;
b. rinsing the hair with water;
wherein the pH of the hair after rinsing is from about 3 to about 6; and
wherein the rinsing of the hair causes one or more of the one to four incipient cations to change from neutral to positively charged inside of the hair shaft,
wherein the chromophore has a structure according to Formula (XI), or a tautomer or salt thereof,

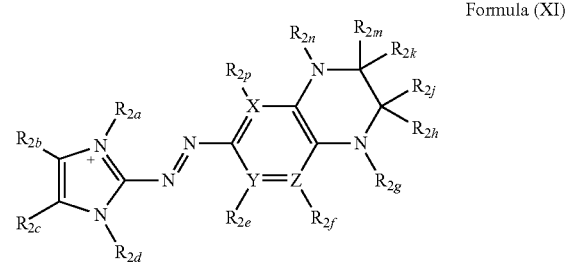

Formula (XI)

wherein
(i) $R_{2h}$, $R_{2j}$, $R_{2k}$ and $R_{2m}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, nitro, nitroso, cyano, a heterocyclic moiety, thioether, thiol with or without a linker group, alkylsulfonate, alkylsulfate, carboxylalkyl, acrylamide or substituted acrylamides with or without a linker group, vinylsulfone with or without a linker group, sulfonyl ethyl sulfate with or without a linker group, halo-s-triazines with or without a linker group, halopyrimidines with or without a linker group, or haloquinoxalines with or without a linker group;
(ii) $R_{2b}$, $R_{2c}$, $R_{2e}$, $R_{2f}$ and $R_{2p}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group; alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, or halopyrimidines with a linker group, haloquinoxalines with a linker group;
(iii) $R_{2g}$ and $R_{2h}$, are each independently hydrogen, alkyl, halogen substituted alkyl, alkenyl, alkynyl, aryl, hydroxyalkyl, aminoalkyl, alkyl group carrying a quaternary ammonium cation, acyl, a heterocyclic moiety, thioether, thiol with a linker group, alkylsulfonate, alkylsulfate, carboxylalkyl; acrylamide or substituted acrylamides with a linker group, vinylsulfone with a linker group, sulfonyl ethyl sulfate with a linker group, halo-s-triazines with a linker group, halopyrimidines with a linker group, or haloquinoxalines with a linker group;
(iv) $R_{2a}$ and $R_{2d}$ are each independently alkyl, halogen substituted alkyl, alkenyl, alkynyl, aryl, hydroxyalkyl, aminoalkyl, alkyl group carrying a quaternary ammonium cation, thioether, thiol with a linker group, alkylsulfonate, alkylsulfate, carboxylalkyl, acrylamide or substituted acrylamides with a linker group, vinyl sulfone with a linker group, sulfonyl ethyl sulfate with a linker group, halo-s-triazines with a linker group, or halopyrimidines with a linker group, haloquinoxalines with a linker group; and
(v) X, Y and Z are each independently a carbon or a nitrogen atom; wherein the total number of nitrogen atoms among X, Y and Z equals to 0 or 1; the total number of carbon atoms among X, Y and Z equals to 2 or 3; and, in the case where one of X, Y, Z is a nitrogen atom, the corresponding group attached to the nitrogen atom, one of $R_{2e}$, $R_{2f}$ or $R_{2p}$, ceases to exist.

5. The method of claim 4, wherein $R_{2a}$ and $R_{2d}$ are each independently alkyl, aminoalkyl or alkyl group carrying a quaternary ammonium cation.

6. The method of claim 4, wherein $R_{2a}$ and $R_{2d}$ are both alkyl groups.

7. The method of claim 4, wherein the hair color composition further comprises from about 0.1% to about 20%, by weight of the composition, of at least one oxidizing agent.

8. A method of dyeing the hair, the method comprising:
a. applying to the hair a hair color composition comprising one or more direct dye compounds, the one or more direct dye compounds each comprising:
i. a blue-violet or blue chromophore;
ii. one or two permanent cations, wherein the permanent cations are pendant to the chromophore or part of the chromophore, and wherein the chromophore and the permanent cations form a core structure; and
iii. one to four incipient cations, wherein each of the one to four incipient cations is pendant via a linker group to the core structure, and wherein the incipient cations are neutral;
iv. one or more C2-C9 hydrophobic moieties, wherein the one or more C2-C9 hydrophobic moieties are pendant to the core structure;

wherein the one or more direct dye compounds enter the hair shaft after the hair color composition is applied to the hair; and
wherein the hair color composition has a pH of from about 6 to about 11;
b. rinsing the hair with water;
wherein the pH of the hair after rinsing is from about 3.5 to about 6; and
wherein the rinsing of the hair causes one or more of the one to four incipient cations to change from neutral to positively charged inside of the hair shaft,
wherein the chromophore has a structure according to Formula (XII), or a tautomer or salt thereof,

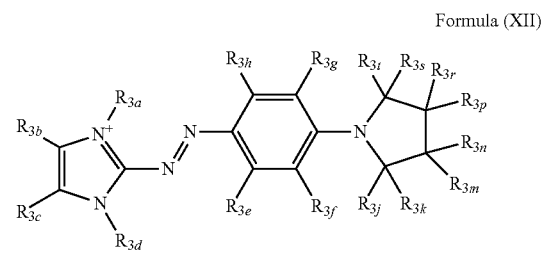

Formula (XII)

wherein
$R_{3f}$, $R_{3k}$, $R_{3m}$, $R_{3n}$, $R_{3p}$, $R_{3r}$, $R_{3s}$, and $R_{3t}$ are each independently hydrogen, alkyl, halogen substituted alkyl, alkenyl, alkynyl, aryl, hydroxyalkyl, aminoalkyl, alkyl group carrying a quaternary ammonium cation, carboxyl, alkoxy, aryloxy, acyl, halogen, nitro, nitroso, cyano, a heterocyclic moiety, thioether, thiol with a linker group, alkylsulfonate, alkylsulfate, carboxylalkyl, acrylamide or substituted acrylamides with or without a linker group, vinylsulfone with or without a linker group, sulfonyl ethyl sulfate with or without a linker group, halo-s-triazines with or without a linker group, halopyrimidines with or without a linker group, or haloquinoxalines with or without a linker group;
(ii) $R_{3b}$, $R_{3c}$, $R_{3e}$, $R_{3f}$, $R_{3g}$, and $R_{3h}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, or haloquinoxalines with a linker group;
(iii) $R_{3a}$ and $R_{3d}$ are each independently, halogen substituted alkyl, alkenyl, alkynyl, aryl, hydroxyalkyl, aminoalkyl, alkyl group carrying a quaternary ammonium cation, thiol with a linker group, alkyl sulfonate, alkylsulfate, carboxylalkyl, acrylamide or substituted acrylamides with a linker group, vinylsulfone with a linker group, sulfonyl ethyl sulfate with a linker group, halo-s-triazines with a linker group, or halopyrimidines with a linker group, haloquinoxalines with a linker group.

9. The method of claim 8, wherein $R_{2a}$ and $R_{2d}$ are each independently, aminoalkyl or alkyl group carrying a quaternary ammonium cation.

10. The method of claim 8, wherein the hair color composition further comprises from about 0.1% to about 20%, by weight of the composition, of at least one oxidizing agent.

* * * * *